US008835683B2

(12) United States Patent
Schneider et al.

(10) Patent No.: US 8,835,683 B2
(45) Date of Patent: Sep. 16, 2014

(54) PROCESS FOR PREPARING FORMIC ACID

(71) Applicant: BASF SE, Ludwigshafen (DE)

(72) Inventors: Daniel Schneider, Mannheim (DE);
Klaus-Dieter Mohl, Hockenheim (DE);
Martin Schäfer, Grünstadt (DE);
Donata Maria Fries, Mannheim (DE);
Joaquim Henrique Teles, Waldsee (DE); Peter Bassler, Viernheim (DE);
Stefan Rittinger, Mannheim (DE);
Thomas Schaub, Neustadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/721,296

(22) Filed: Dec. 20, 2012

(65) Prior Publication Data

US 2013/0190532 A1    Jul. 25, 2013

Related U.S. Application Data

(60) Provisional application No. 61/577,703, filed on Dec. 20, 2011.

(51) Int. Cl.
*C07C 51/44* (2006.01)
*C07C 51/02* (2006.01)

(52) U.S. Cl.
CPC .............. *C07C 51/44* (2013.01); *C07C 51/02* (2013.01)
USPC ...................................................... 562/609

(58) Field of Classification Search
None
See application file for complete search history.

(56) References Cited

U.S. PATENT DOCUMENTS

| 4,217,460 | A | 8/1980 | Hohenschutz et al. |
| 4,218,568 | A | 8/1980 | Hohenschutz et al. |
| 5,294,740 | A | 3/1994 | Kiefer et al. |
| 2008/0097126 | A1 | 4/2008 | Karl et al. |
| 2010/0063320 | A1 | 3/2010 | Challand et al. |
| 2010/0126843 | A1 | 5/2010 | Stabel et al. |

FOREIGN PATENT DOCUMENTS

| CA | 2774151 A1 | 1/2012 |
| DE | 2545658 A1 | 4/1977 |
| DE | 3428319 A1 | 2/1986 |
| DE | 102009046310 A1 | 5/2010 |
| EP | 0 001 432 A1 | 4/1979 |
| EP | 0126524 A1 | 11/1984 |
| EP | 0181078 A1 | 5/1986 |
| EP | 0563831 A2 | 10/1993 |
| WO | WO-2006/021411 A1 | 3/2006 |
| WO | WO-2008/116799 A1 | 10/2008 |
| WO | WO 2010149507 | * 12/2010 |
| WO | PCT/EP2011/060012 | 1/2012 |
| WO | PCT/EP2011/060770 | 1/2012 |
| WO | WO-2012000799 A1 | 1/2012 |
| WO | WO-2012000964 A1 | 1/2012 |

OTHER PUBLICATIONS

U.S. Appl. No. 13/172,123, filed Jun. 29, 2011, Schaub et al.
U.S. Appl. No. 13/171,928, filed Jun. 29, 2011, Schaub et al.
U.S. Appl. No. 61/316,841.
U.S. Appl. No. 13/171,598, filed Jun. 29, 2011, Schneider et al.
U.S. Appl. No. 61/392,062.
U.S. Appl. No. 13/330,974, filed Dec. 20, 2011, Schaub et al.
U.S. Appl. No. 13/542,791.
U.S. Appl. No. 61/532,579.
U.S. Appl. No. 13/559,011.
U.S. Appl. No. 13/646,161.
U.S. Appl. No. 61/577,701.
U.S. Appl. No. 61/557,931.

* cited by examiner

*Primary Examiner* — Brandon Fetterolf
*Assistant Examiner* — Ana Z Muresan
(74) *Attorney, Agent, or Firm* — Drinker Biddle & Reath LLP

(57) ABSTRACT

Process for obtaining formic acid by thermal separation of a stream comprising formic acid and a tertiary amine (I), in which a liquid stream comprising formic acid, tertiary amine (I) and water is produced by combining tertiary amine (I) and a formic acid source in the presence of water, water and organic decomposition products of the tertiary amine (I) are removed and formic acid is removed by distillation from the resulting liquid stream in a distillation apparatus, wherein the stream comprising water and organic decomposition products of the tertiary amine (I) which have been separated off is separated into two liquid phases, the upper liquid phase is removed and the lower, water-comprising liquid phase is recirculated to the formic acid source.

10 Claims, 13 Drawing Sheets

(a)

(b)

(c)

Examples 1 and 2

PROCESS FOR PREPARING FORMIC ACID

RELATED APPLICATIONS

This application claims benefit (under 35 USC 119(e)) of U.S. Provisional Application Ser. No. 61/577,703, filed Dec. 20, 2011, which is incorporated herein by reference in its entirety.

BACKGROUND OF THE INVENTION

The present invention relates to a process for obtaining formic acid by thermal separation of a stream comprising formic acid and a tertiary amine (I), in which a liquid stream comprising formic acid, tertiary amine (I) and water in a molar ratio of formic acid to tertiary amine (I) of from 0.5 to 5 is produced by combining tertiary amine (I) and a formic acid source in the presence of water, water and organic decomposition products of the tertiary amine (I) are removed and formic acid is removed by distillation at a temperature at the bottom of from 100 to 300° C. and a pressure of from 30 to 3000 hPa abs from the resulting liquid stream in a distillation apparatus.

Formic acid is an important and versatile product. It is used, for example, for acidification in the production of animal feeds, as preservative, as disinfectant, as assistant in the textile and leather industry, in the form of its salts for deicing aircraft and runways and also as synthetic building block in the chemical industry.

The most widespread process at present for preparing formic acid is the hydrolysis of methyl formate which can be obtained, for example, from methanol and carbon monoxide. The aqueous formic acid obtained by hydrolysis is subsequently concentrated, for example using an extraction auxiliary such as a dialkylformamide (DE 25 45 658 A1).

In addition, obtaining formic acid by thermal dissociation of compounds of formic acid and a tertiary nitrogen base is also known. These compounds are generally acidic ammonium formates of tertiary nitrogen bases, in which the formic acid has reacted beyond the stage of classical salt formation with the tertiary nitrogen bases to form stable addition compounds bridged by hydrogen bonds. The addition compounds of formic acid and tertiary nitrogen bases can be formed by combining the tertiary nitrogen base and a formic acid source. Thus, for example, WO 2006/021,411 discloses the preparation of such addition compounds in general by (i) direct reaction of the tertiary nitrogen base with formic acid, (ii) by transition metal-catalyzed hydrogenation of carbon dioxide to formic acid in the presence of the tertiary nitrogen base, (iii) by reaction of methyl formate with water and subsequent extraction of the resulting formic acid by means of the tertiary nitrogen base and (iv) by reaction of methyl formate with water in the presence of the tertiary nitrogen base.

The general advantages of using addition compounds of formic acid and tertiary nitrogen bases for obtaining formic acid are that the addition compounds firstly bind the formic acid strongly enough to withdraw the formic acid as free formic acid from the medium, for example the reaction medium, in which the formic acid has been formed by chemical synthesis or, for example, from a dilute formic acid solution and thereby allow the formic acid to be separated off more readily in the form of its addition compounds, but are weak enough for the formic acid subsequently to be able to be released again from the addition compounds by thermal dissociation in order to obtain it in concentrated and purified free form.

EP 0 001 432 A discloses a process for obtaining formic acid by hydrolysis of methyl formate in the presence of a tertiary amine, in particular an alkylimidazole, to form addition compounds of formic acid and the tertiary amine. The hydrolysis mixture obtained, which comprises unreacted methyl formate, water, methanol, addition compounds and tertiary amine, is freed of the low boilers methyl formate and methanol in a first distillation column. In a second column, the remaining bottom product is dewatered. The dewatered bottom product from the second column, which still comprises addition compounds and tertiary amine, is then fed to a third column and in this the addition compounds are thermally dissociated into formic acid and tertiary amine. The formic acid liberated is removed as overhead product. The tertiary amine collects in the liquid phase and is recirculated to the hydrolysis.

DE 34 28 319 A discloses a process for obtaining formic acid by hydrolysis of methyl formate. The hydrolysis mixture obtained, which comprises unreacted methyl formate, water, methanol and formic acid, is freed of the low boilers methyl formate and methanol in a first distillation column. The aqueous formic acid obtained at the bottom is subsequently extracted with a relatively high-boiling amine, in particular a relatively long-chain, hydrophobic $C_6$-$C_{14}$-trialkylamine, in the presence of an additional hydrophobic solvent, in particular an aliphatic, cycloaliphatic or aromatic hydrocarbon, and thereby converted into an aqueous addition compound of formic acid and the amine. This is dewatered in a second distillation column. The dewatered addition compound obtained at the bottom is then, according to the teaching of DE 34 28 319 A, fed to the uppermost plate of a distillation column (in FIG. 1 denoted as "K4") and thermally dissociated. The hydrophobic solvent is present both in the overhead stream and the bottoms from the column. The gaseous overhead stream comprises mainly the formic acid liberated together with the hydrophobic solvent. This stream is liquefied again in the condenser. This results in formation of two phases, namely a polar formic acid phase and a hydrophobic solvent phase. The formic acid phase is discharged as product and the solvent phase is returned as runback to the column. Due to the presence of the hydrophobic solvent, complete dissociation of the adduct, which according to the teaching of the DE first publication occurs without decomposition of formic acid, can be achieved. The (virtually) formic acid-free bottoms comprise the hydrophobic amine and the hydrophobic solvent. This is recirculated to the extraction stage.

EP 0 181 078 A and EP 0 126 524 A describe processes for obtaining formic acid by hydrogenation of carbon dioxide in the presence of a transition metal catalyst and a tertiary amine such as a $C_1$-$C_{10}$-trialkylamine to form an addition compound of formic acid and the tertiary amine, work-up of the hydrogenation output to separate off the catalyst and the low boilers, replacement of the amine base by a weaker, higher-boiling tertiary amine, in particular by an alkylimidazole, with splitting-off of the first tertiary amine and subsequent thermal dissociation of the newly formed addition compound in a distillation column. According to EP 0 181 078 A, FIG. 1, the stream comprising formic acid and amine is for this purpose fed into the middle region of the column "30". The formic acid liberated in the thermal dissociation is removed as overhead product. The weaker, higher-boiling tertiary amine collects at the bottom and is recirculated to the stage of base exchange.

WO 2008/116,799 discloses a process for obtaining formic acid by hydrogenation of carbon dioxide in the presence of a transition metal catalyst, a high-boiling polar solvent such as an alcohol, ether, sulfolane, dimethyl sulfoxide or amide and a polar amine bearing at least one hydroxyl group to form an addition compound of formic acid and the amine. According to the teaching of WO 2008/116,799, the hydrogenation output can be fed directly to a distillation apparatus for thermal dissociation of the addition compound. This can comprise a distillation column and, if short residence times are desired, also a thin film evaporator or falling film evaporator. The formic acid liberated is removed as overhead product. The polar amine and the polar solvent and any catalyst which has not been separated off collect at the bottom and can be recirculated to the hydrogenation stage.

WO 2006/021,411 describes a process for obtaining formic acid by thermal dissociation of an addition compound of formic acid and a tertiary amine (quaternary ammonium formate), in which the tertiary amine has a boiling point of from 105 to 175° C. Alkylpyridines are mentioned as preferred tertiary amines. The specific boiling range of the tertiary amines increases the color stability of the formic acid obtained. The addition compound to be used can in general be obtained from the tertiary amine and a formic acid source. The output from the adduct synthesis is advantageously firstly freed of volatile constituents and then fed to the thermal dissociation. The thermal dissociation is carried out as usual in a distillation column, with the stream comprising formic acid and amine being fed as per FIG. 1 of WO 2006/021,411 into the middle region of the column (C). The formic acid liberated is removed as overhead product. The tertiary amine which may still comprise residues of formic acid collects in the liquid phase and can be recirculated to the formic acid source.

EP 0 563 831 A reports an improved process for the thermal dissociation of an addition compound of formic acid and a tertiary amine (quaternary ammonium formate) to give formic acid. The addition compound to be used can in general be obtained from the tertiary amine and a formic acid source. The output from the synthesis is advantageously firstly freed of volatile constituents and then fed into the middle of a distillation column for thermal dissociation. The improvement comprises essentially carrying out the thermal dissociation of the addition compound in the presence of a secondary formamide which increases the color stability of the formic acid obtained. The formic acid liberated is removed as overhead product. The tertiary amine and the secondary formamide collect in the liquid phase and can be recirculated to the formic acid source.

PCT/EP2011/060770 teaches a process for obtaining formic acid by thermal separation of a stream comprising formic acid and a tertiary amine (I), in which combining tertiary amine (I) and a formic acid source produces a liquid stream comprising formic acid and a tertiary amine (I) in a molar ratio of from 0.5 to 5, from 10 to 100% by weight of the secondary components comprised therein are separated off and formic acid is removed by distillation from the resulting liquid stream in a distillation apparatus at a temperature at the bottom of from 100 to 300° C. and a pressure of from 30 to 3000 hPa, and the bottom output from the distillation apparatus is separated into two liquid phases of which the upper liquid phase is enriched in tertiary amine (I) and is recirculated to the formic acid source and the lower liquid phase is enriched in formic acid and is recirculated to removal of the secondary components and/or to the distillation apparatus.

It is an object of the present invention to discover an improved process for obtaining formic acid by thermal separation of a stream comprising formic acid and a tertiary amine, which process has advantages over the prior art and is able to give formic acid in high yield and high concentration. In particular, the improved process should also function stably over long operating times and produce formic acid in constant high purity. The process should naturally be able to be carried out very simply and with a very low energy consumption.

We have surprisingly found a process for obtaining formic acid by thermal separation of a stream comprising formic acid and a tertiary amine (I) which at a pressure of 1013 hPa abs has a boiling point which is at least 5° C. higher than that of formic acid, in which (a) a liquid stream comprising formic acid, tertiary amine (I) and water and having a molar ratio of formic acid to tertiary amine (I) of from 0.5 to 5 is produced by combining tertiary amine (I) and a formic acid source in the presence of water;

(b) water and organic decomposition products of the tertiary amine (I) are separated off from the liquid stream obtained from step (a), with the organic decomposition products of the tertiary amine (I) having been comprised in the tertiary amine (I) fed to step (a) and/or been formed during the course of the process up to the present step (b), and a liquid stream which comprises formic acid and tertiary amine (I) and is depleted in water and organic decomposition products of the tertiary amine (I) is obtained; and (c) formic acid is removed by distillation from the liquid stream comprising formic acid and tertiary amine (I) obtained from step (b) in a distillation apparatus at a temperature at the bottom of from 100 to 300° C. and a pressure of from 30 to 3000 hPa abs;

wherein (b1) the stream comprising water and organic decomposition products of the tertiary amine (I) which has been separated off in step (b) is separated into two liquid phases;

(b2) the upper liquid phase enriched in organic decomposition products of the tertiary amine (I) is removed; and (b3) the lower, water-comprising liquid phase is recirculated to step (a).

A BRIEF DESCRIPTION OF THE FIGURES

A DETAILED DESCRIPTION OF THE INVENTION

Figure 1:
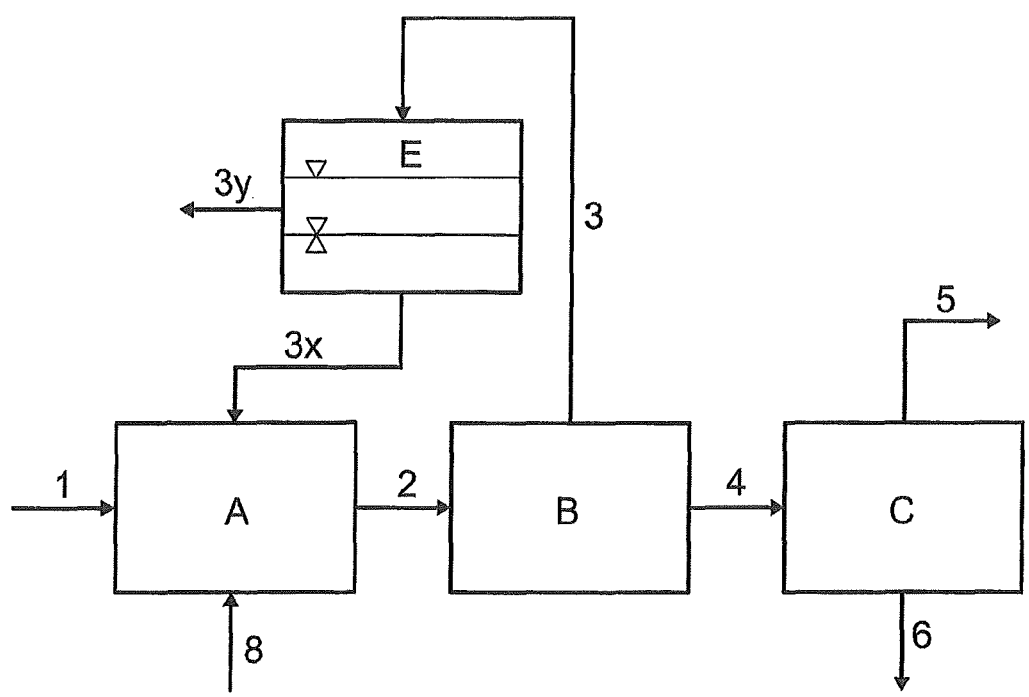
FIG. 1 shows a simplified block diagram of a general embodiment of the process of the invention.

The tertiary amine (I) used in step (a) of the process of the invention has, at a pressure of 1013 hPa abs, a boiling point which is at least 5° C. higher than that of formic acid. The tertiary amine (I) to be used preferably has a boiling point which is at least 10° C. higher, particularly preferably at least 50° C. higher and very particularly preferably at least 100° C. higher, than that of formic acid. A restriction in respect of an upper limit value for the boiling point is not necessary since a very low vapor pressure of the tertiary amine (I) is basically advantageous for the process of the invention. In general, the boiling point of the tertiary amine (I) is below 500° C. at a pressure optionally extrapolated by known methods from vacuum to 1013 hPa abs.

The formic acid source mentioned in step (a) is a stream which comprises formic acid in dilute, contaminated and/or chemically bound form or comprises a precursor from which formic acid is produced by chemical reaction. The formic acid source in step (a) ultimately ensures the direct or indirect introduction of formic acid. Addition in chemically bound form can, for example, be effected in the form of a complex, a salt or an addition compound of formic acid and an amine other than the tertiary amine (I). Possible chemical reactions are in principle all chemical reactions in which formic acid is produced. However, the production of formic acid by hydrolysis of methyl formate and production of formic acid by transition metal-catalyzed hydrogenation of carbon dioxide are of particular industrial importance at the time of the present patent application. Both the possible syntheses mentioned are well known in the art and have been described in a variety of variants and embodiments. A further industrially relevant possibility for producing formic acid by chemical reaction is, for example, direct reaction of carbon monoxide with water.

In the case of the hydrolysis of methyl formate, it is usual to introduce methyl formate, water and tertiary amine (I) either together or in succession into the hydrolysis reactor in order to trap the formic acid formed by hydrolysis in the form of an addition compound by means of the tertiary amine (I) and thus withdraw it from the hydrolysis equilibrium. This makes it possible to achieve a higher conversion of methyl formate and allows particularly advantageous removal of the unreacted water by means of a subsequent distillation.

In the case of the transition metal-catalyzed hydrogenation of carbon dioxide, the tertiary amine (I) is generally introduced into the hydrogenation reactor in order to form a stream comprising formic acid and a tertiary amine (I) in the hydrogenation itself.

The stream comprising formic acid and tertiary amine (I) is preferably produced by hydrolysis of methyl formate in the presence of water and tertiary amine (I) in step (a). Production of the stream comprising formic acid and tertiary amine (I) by concentration of dilute formic acid in the presence of tertiary amine (I) in step (a) is also preferred. However, the stream comprising formic acid and tertiary amine (I) is particularly preferably produced by hydrolysis of methyl formate in the presence of water and tertiary amine (I) in step (a).

The content of water on combining the tertiary amine (I) and the formic acid source in step (a) should be set so that the liquid stream produced in step (a) comprises not only formic acid and tertiary amine (I) but also water. In determining the amount of water to be used, it is thus necessary to take into account whether, in the case of the addition of a formic acid source which comprises formic acid in chemically bound form or comprises a precursor from which formic acid is produced only by chemical reaction, water is or is not also required for the liberation of formic acid. Thus, for example, when formic acid is prepared from carbon monoxide and water and naturally also in the preferred hydrolysis of methyl formate, water is in each case consumed chemically for preparing the formic acid. Correspondingly, the amount of chemically consumed water has to be taken into account in determining the addition of water.

The combining of tertiary amine (I) and the formic acid source can be carried out in a variety of ways. If the formic acid source is a stream comprising formic acid in dilute, contaminated and/or chemically bound form, simple contacting, preferably with mixing, with the tertiary amine (I) is often sufficient. This can, for example, be carried out in tubes which preferably comprise suitable mixing internals. Contacting can likewise be carried out in other apparatuses, for example stirred vessels. Stepwise combining in which the tertiary amine (I) is added stepwise to the formic acid source or, conversely, the formic acid source is added stepwise to the tertiary amine (I) is also possible and may even be advantageous. If the formic acid source is a stream from which the formic acid is to be produced from a number of materials by chemical reaction, it is generally advantageous to produce the formic acid source by combining the individual components in the reactor. Possible reactors are, in particular, the reactors known to those skilled in the art for this type of reaction. The tertiary amine (I) can, for example, be initially charged, introduced in parallel to the individual components of the formic acid source, introduced during the course of the chemical reaction or introduced only at the end of the chemical reaction. It is also possible to distribute these individual steps over a plurality of reactors. Depending on the heat involved on combining tertiary amine (I) and the formic acid source, it may be advantageous to cool the apparatus itself or the stream obtained therefrom.

Suitable ways of combining tertiary amine (I) and the formic acid source can be determined without great difficulty on the basis of routine knowledge in the art.

The liquid stream produced on combining tertiary amine (I) and a formic acid source in step (a) has a molar ratio of formic acid to tertiary amine (I) of from 0.5 to 5. The molar ratio is preferably ≥1 and preferably ≤3. The molar ratio mentioned is based on the total liquid stream, regardless of whether it is present as a single phase or a plurality of phases.

The liquid stream comprising formic acid, tertiary amine (I) and water which is produced in step (a) generally has a concentration of formic acid plus tertiary amine (I) of from 1 to 99% by weight, based on the total amount of the stream. The stream mentioned preferably has a concentration of formic acid plus tertiary amine (I) of ≥5% by weight and particularly preferably ≥15% by weight and also preferably ≤95% by weight and particularly preferably ≤90% by weight. The remaining part to 100% by weight of the stream is composed of water, possibly organic decomposition products of the tertiary amine (I) and secondary components as will be defined in the further course of the present description. Based on this remaining part, the proportion by weight of water is generally from 1 to <100%, preferably 5% and particularly preferably 10% and also preferably ≤99% and particularly preferably ≤95%.

It is appropriate to separate off water from the liquid stream comprising formic acid and tertiary amine (I) and also water which is obtained from step (a) in order to concentrate the formic acid. In the context of the present invention, it has surprisingly been found that it is possible and also particularly advantageous to separate off not only the water but also organic decomposition products of the tertiary amine (I) in this step. For this reason, water and organic decomposition products of the tertiary amine (I) are separated off in step (b) of the process of the invention from the liquid stream obtained in step (a), with the organic decomposition products of the tertiary amine (I) having been present in the tertiary amine (I) fed to step (a) and/or having been formed during the course of the process up to the present step (b), to give a liquid stream which comprises formic acid and tertiary amine (I) and is depleted in water and organic decomposition products of the tertiary amine (I).

For the purposes of the present invention, the term organic decomposition products of the tertiary amine (I) refers to compounds which are formed by chemical transformation of the tertiary amine (I) with parting of bonds originally present, new formation of nitrogen-carbon bonds or chemical transformation of the radicals bound to the nitrogen. Thus, it has been recognized in the context of the invention that tertiary amines (I) tend, for example, to decompose in the presence of formic acid at elevated temperature and elevated pressure, as prevail in individual steps of the process of the invention, to form the corresponding formamide which is N,N-substituted by the radicals of the tertiary amine (I) and the corresponding formate comprising the other radical of the tertiary amine (I). In the case of a tertiary amine (I) having three identical radicals R, for example $C_5$-$C_8$-alkyl, the abovementioned decomposition reaction would, for example, be as follows:

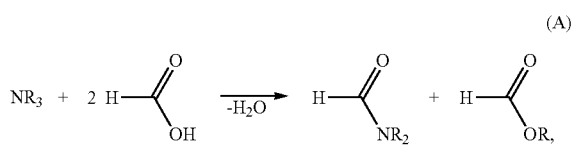

(A)

forming the corresponding dialkylformamide and the corresponding alkyl formate as organic decomposition products of the tertiary amine (I). Furthermore, it has been recognized in the context of the invention that tertiary amines (I) also tend, for example, to decompose in the presence of formic acid and traces of oxygen at elevated temperature, as can prevail in individual steps of the process of the invention, to form the corresponding formamide which is N,N-substituted by the radicals of the tertiary amine (I) and the aldehyde formed from the other radical. In the case of a tertiary amine (I) having three identical radicals $CH_2$—R, for example $C_5$-$C_8$-alkyl, the above-mentioned decomposition reaction would, for example, be as follows:

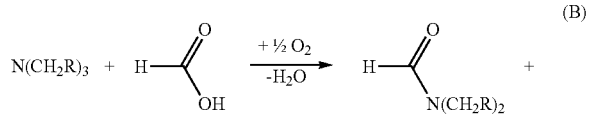

(B)

-continued

forming the corresponding dialkylformamide and the corresponding alkanal as organic decomposition products of the tertiary amine (I).

The organic decomposition products of the tertiary amine (I) to be separated off in the process of the invention are either present in the tertiary amine (I) fed to step (a) and/or are formed only during the course of the process up to the present step (b). Thus, it is, for example, possible for the tertiary amine (I) fed to step (a) to comprise various organic decomposition products of the tertiary amine (I) as a result of its production or pretreatment. This is generally the case when the tertiary amine (I) obtained after the removal of formic acid by distillation in step (c) is recirculated to step (a). However, it is also possible for the organic decomposition products of the tertiary amine (I) to be separated off to be formed, either exclusively or in addition to those introduced in the tertiary amine (I), only in step (a) under appropriate conditions and/or only in the removal of the water in step (b) and/or in optional intermediate steps between step (a) and step (b).

The amount of organic decomposition products of the tertiary amine (I) which are usually separated off in step (b) of the process of the invention can be very different depending on the way in which the process is carried out. Critical factors here are, in particular, the purity of the tertiary amine (I) used, whether the tertiary amine (I) obtained in step (c) is or is not recirculated, the further conditions in the process (e.g. temperature, pressure, presence of oxygen, concentration ratios, etc., in the individual process steps). In general, an amount of organic decomposition products of the tertiary amine (I) corresponding to from 5 ppm by weight to 5% by weight of the amount of the total stream fed to step (b) is separated off in step (b) of the process of the invention. Here, the total stream is the entire stream fed to step (b), i.e. including formic acid, tertiary amine (I), water and any further components. Preference is given to separating off ≥10 ppm by weight and particularly preferably ≥30 ppm by weight and also preferably ≤2% by weight and particularly preferably ≤1% by weight.

The organic decomposition products of the tertiary amine (I) can have disadvantageous effects on the process if they are not separated off according to the invention. Thus, they can, for example, depending on the type and concentration, have an adverse effect on the purity of the formic acid obtained by distillation in step (c) or make necessary a more complicated distillation apparatus (necessity of a large number of theoretical plates) or even a separate after-distillation in order to ensure a high purity in, for example, step (c). Furthermore, the organic decomposition products of the tertiary amine (I) can, in the event of recirculation of the tertiary amine (I) obtained after the removal of formic acid by distillation in step (c) to step (a), accumulate in the process and significantly increase the above-described disadvantageous effect in respect of the purity of the formic acid obtained. In addition, it has surprisingly been found, in the context of the present invention, that in a further particularly preferred variant which is described further below in the text and in which the bottoms from the distillation apparatus of step (c) is separated into two phases which are separately recirculated to separate places in the process, the quality of the phase separation suffers with increasing content of organic decomposition products of the tertiary amine (I) and the two phases increasingly mix or, in the extreme case, phase separation does not occur at all. As a result, a higher content of the undesirable component is transported in the two recycle streams, which leads to a general increase in the flows in the process and thus ultimately to larger apparatuses and lines and also to an increased energy consumption for operation.

Furthermore, it has surprisingly been found in the context of the present invention that the stream comprising water and organic decomposition products of the tertiary amine (I) which is separated off in step (b) separates into two liquid phases. Step (b1) of the present invention therefore comprises separation of the stream comprising water and organic decomposition products of the tertiary amine (I) which is separated off in step (b) into two liquid phases. The upper liquid phase which is enriched in organic decomposition products of the tertiary amine (I) is removed in step (b2) and the lower, water-comprising liquid phase is recirculated to step (a) in step (b3). The removal of the upper liquid phase which is enriched in organic decomposition products of the tertiary amine (I) in step (b2) can, for example, be carried out continuously or discontinuously. The output comprising organic decomposition products of the tertiary amine (I) can then, for example, be disposed of, with thermal utilization also coming into question. However, it may also be possible to use the output as feed or raw material for syntheses.

The separation in step (b) of water and organic decomposition products of the tertiary amine (I) from the liquid stream obtained in step (a) is preferably carried out by distillation. Possible distillation apparatuses for this purpose are in principle apparatuses which are known to those skilled in the art for such separation tasks or can be designed by a person skilled in the art using general technical knowledge. The temperature at the bottom is advantageously in the range from 100 to 300° C., preferably from 120 to 290° C., particularly preferably from 150 to 280° C., and the pressure is advantageously in the range from 100 to 4000 hPa abs.

In step (b), further components which will in the following be referred to as secondary components in the interests of simplicity can naturally also be separated off in addition to water and organic decomposition products of the tertiary amine (I) from the liquid stream obtained in step (a). Here, the term secondary components refers to all components which are comprised in the liquid stream obtained in step (a) and are not formic acid, tertiary amine (I), water or organic decomposition products of the tertiary amine (I). Examples which may be mentioned are methanol (in particular in the case of the hydrolysis of methyl formate), anhydrolyzed methyl formate (in particular in the case of the hydrolysis of methyl formate), dissolved inert gases, homogeneous catalyst (in particular in the case of the hydrogenation of carbon dioxide), dissolved carbon dioxide or dissolved hydrogen (in particular in the case of the hydrogenation of carbon dioxide), solvents, other components.

The way in which the secondary components may be separated off if required is inconsequential for the process of the invention. Thus, for example, it is possible to use the customary and known methods for the separation of liquid mixtures. Particular mention may be made of separation by distillation. Thus, for example, low-boiling secondary components such as methanol or methyl formate can be separated off at the top or as a side offtake stream from a distillation apparatus. However, it is also conceivable to separate off high-boiling secondary components at the bottom and the mixture comprising formic acid and tertiary amine (I) as side stream or overhead product. Apart from separation by distillation, membrane, absorption, adsorption, crystallization, filtration, sedimentation or extraction processes are also possible.

It is naturally also possible to combine a plurality of separation steps which may also be based on different methods. The design of the separation step or separation steps can be undertaken using conventional technical knowledge.

The possible removal of secondary components in step (b) can in principle be carried out before or after the removal of water and organic decomposition products of the tertiary amine (I). Critical factors in determining the order are predominantly practical aspects and, when one or more distillation steps is/are used, the corresponding materials properties. When methanol and/or unreacted methyl formate is/are separated off by distillation when using methyl formate as formic acid source, they are, owing to the position of the boiling points, separated off before the removal of water and organic decomposition products of the tertiary amine (I), for example likewise by distillation.

The amount of water separated off in step (b) is, in the process of the invention, generally from 10 to 100% of the amount of water comprised in the stream from step (a). Preference is given to ≥20% and particularly preferably ≥30% and also preferably ≤97% and particularly preferably ≤95% of the amount of water comprised in the stream from step (a) being separated off in step (b).

Of course, further process steps apart from step (b) can be carried out between steps (a) and (c) in the process of the invention.

Finally, formic acid is removed by distillation in a distillation apparatus at a temperature at the bottom of from 80 to 300° C., preferably from 100 to 300° C., and a pressure of from 30 to 3000 hPa abs from the liquid stream obtained from step (b). As distillation apparatuses for this purpose, it is in principle possible to use the apparatuses known to those skilled in the art for such separation tasks or can be designed by a person skilled in the art using general technical knowledge.

The distillation apparatus usually comprises not only the actual column body with internals but also, inter alia, an overhead condenser and a bottom vaporizer. In addition, these can naturally also comprise further peripheral apparatuses or internals, for example a flash vessel in the feed line (for example to separate gas and liquid in the feed to the column body), an intermediate vaporizer (for example for improved heat integration of the process) or internals for avoiding or reducing aerosol formation (for example heatable trays, demisters, coalescers or deep-bed diffusion filters). The column body can be equipped, for example, with ordered packing, random packing elements or trays. The number of theoretical plates required is dependent, in particular, on the type of tertiary amine (I), the concentration of formic acid and tertiary amine (I) in the feed to the distillation apparatus in step (c) and the desired concentration or the desired purity of the formic acid, and can be determined in a conventional way by a person skilled in the art. The number of theoretical plates required is generally ≥3, preferably ≥6 and particularly preferably ≥7. There are in principle no upper limits. However, for practical reasons it will be usual to use generally ≤70, optionally ≤50, theoretical plates or even ≤30 theoretical plates.

The stream comprising formic acid and tertiary amine (I) from step (b) can be fed, for example, as side stream to the column body in the distillation apparatus.

A flash evaporator, for example, can optionally also precede the addition. To keep the thermal stress on the stream fed into the distillation apparatus as small as possible, it is generally advantageous to feed this in in a relatively low region of the distillation apparatus. Thus, in step (c), the stream comprising formic acid and tertiary amine (I) is preferably fed in in the region of the lower quarter, preferably in the region of the lower fifth and particularly preferably in the region of the lower sixth, of the theoretical plates present, with direct introduction into the bottom naturally also being comprised here.

As an alternative, preference is also given, in step (c), to feed said stream comprising formic acid and a tertiary amine (I) from step (b) into the bottom vaporizer of the distillation apparatus.

The distillation apparatus is operated at a temperature at the bottom of from 100 to 300° C. and a pressure of from 30 to 3000 hPa abs. The distillation apparatus is preferably operated at a temperature at the bottom of ≥120° C., particularly preferably ≥140° C., and preferably ≤220° C. and particularly preferably ≤200° C. The pressure is preferably ≥30 hPa abs, particularly preferably ≥60 hPa abs, and preferably ≤1500 hPa abs and particularly preferably ≤500 hPa abs.

Depending on the composition and origin of the feed comprising formic acid and a tertiary amine (I) to the distillation apparatus, formic acid can be obtained as overhead product and/or side product from the distillation apparatus. If the feed comprises constituents having boiling points lower than that of formic acid, it may be advantageous to separate these off as overhead product and separate off the formic acid at a side offtake in the distillation. In the case of possible dissolved gases (for example carbon monoxide or carbon dioxide) in the feed, it is generally also possible to separate off the formic acid together with these as overhead product. If the feed comprises constituents having boiling points higher than that of formic acid, formic acid is preferably separated off by distillation as overhead product, but optionally instead or additionally in the form of a second stream at the side offtake. The constituents which have boiling points higher than that of formic acid are in this case preferably taken off in an additional side stream. The side stream comprising secondary components can optionally be recirculated to step (b) in order to separate off the secondary components.

Formic acid having a content of up to 100% by weight can be obtained in this way. In general, formic acid contents of from 75 to 99.995% by weight can be achieved without problems. The balance to 100% by weight is mainly water, with other components such as solvents or possible decomposition products naturally also being conceivable as materials apart from formic acid and the tertiary amine (I) introduced into the distillation apparatus. Thus, water can, for example, be comprised in the feed to the distillation apparatus or else may also be formed in small amounts only in the thermal separation by decomposition of formic acid.

In the isolation of concentrated formic acid having a content of from 95 to 100% by weight as overhead or side product, water is discharged in a side stream together with part of the formic acid split off. The formic acid content of the side stream is typically from 75 to 95% by weight. The aqueous formic acid in the side stream can optionally be recirculated to step (b) in order to separate off the water.

However, it is also possible to discharge the water and the formic acid split off in a joint overhead or side stream. The formic acid content of the product obtained in this way is then generally from 85 to 95% by weight.

To largely suppress, in particular, the formation of organic decomposition products of the tertiary amine (I) which are formed by oxidation, it is particularly advantageous, especially when the distillation apparatus is operated at pressures below 0.1 MPa abs, for the intrusion of oxygen through a large number of connections, ports and flanges to be avoided or at least kept extremely low by special care during installation, by use of particularly well-sealed flange connections (for instance those having comb profile seals or weld lip seals) or by means of nitrogen-blanketed flange connections. A suitable flange connection is disclosed, for example, in DE 10 2009 046 310 A1.

The formic acid which can be obtained by the process of the invention has a low color number and also a high color number stability. In general, a color number of ≤20 APHA, in particular even ≤10 APHA and possibly even ≤5 APHA, can be achieved without problems. Even on storage for a number of weeks, the color number remains virtually constant or increases only insignificantly.

Owing to the removal of the organic decomposition products of the tertiary amine (I) according to the invention in step (b), a particularly pure formic acid in which said decomposition products are generally present in a concentration of ≤70 ppm by weight, preferably ≤30 ppm by weight and very particularly preferably ≤20 ppm by weight, can be obtained without a further outlay.

The content of secondary components is also extremely low and is generally ≤100 ppm by weight, preferably ≤50 ppm by weight and very particularly preferably ≤25 ppm by weight.

It may also be advantageous to use a plurality of distillation apparatuses in step (c), particularly when further fractions, for example accompanying materials comprised, reaction by-products, impurities and/or formic acid fractions of various purities and concentrations, are to be obtained in addition to the free formic acid and the amine (I)-comprising bottom product.

The distillation apparatus for separating off the formic acid can naturally also be configured as thermally coupled distillation columns or as a dividing wall column.

In a preferred variant of the process of the invention, (i) a formic acid source which comprises methyl formate and from which a liquid stream comprising formic acid, tertiary amine (I), water and methanol is obtained by hydrolysis of methyl formate is used in step (a), and (ii) a further stream comprising the methanol formed from the dissociation of methyl formate is separated in step (b) from the stream obtained from step (a). The methanol which has been separated off can then, for example, be reused in the synthesis of methyl formate. Since methanol has a significantly lower boiling point than water and can thus be separated off relatively easily by distillation from a corresponding mixture comprising methanol, water, formic acid and tertiary amine (I), it is advantageous in this variant to separate off methanol straight away as separate stream from the stream obtained from step (a).

If methanol is separated off in the variant described in the previous paragraph, it is particularly advantageous (i) in step (b) to separate off, likewise straight away, a further stream comprising unreacted methyl formate from the stream obtained from step (a) and (ii) to recirculate the methyl formate which has been separated off to step (a). In this way, the yield of formic acid based on the methyl formate used can be increased significantly. Since methyl formate has a significantly lower boiling point than methanol and can thus be separated off even more easily by distillation from a corresponding mixture comprising methyl formate, methanol, water, formic acid and tertiary amine (I), it is advantageous in this variant to separate off methyl formate and methanol straight away as separate streams from the stream obtained from step (a). This can, for example, be carried out in two separate distillation apparatuses in which methyl formate is separated off in the first column and methanol is separated off in the second column. However, it is also possible, for example, to separate off the two components in separate streams in a single distillation apparatus. For example, methyl formate can be obtained as overhead product and methanol can be obtained as side stream product.

The hydrolysis of methyl formate in step (a) usually takes place in a temperature range from 80 to 150° C. and a pressure range from 0.4 to 25 MPa abs. It is in principle possible to use all apparatuses in which an exothermic reaction of fluid streams is possible as apparatus for carrying out the hydrolysis in step (a). Examples which may be mentioned are stirred vessels, tube reactors or shell-and-tube reactors, in each case without internals or with internals (for example beds, packing elements, perforated plates and the like). The hydrolysis is preferably carried out adibatically or with removal of heat.

In another preferred variant of the process of the invention, (i) a formic acid source which comprises carbon dioxide, hydrogen and a homogeneous catalyst and from which a liquid stream comprising formic acid, tertiary amine (I), water and methanol is obtained by homogeneously catalyzed hydrogenation of carbon dioxide is used in the presence of methanol in step (a) and (ii) a further stream comprising methanol is separated off in step (b) from the stream obtained from step (a) and the methanol which has been separated off is recirculated to step (a). In this variant, methanol and water serve first and foremost as polar solvents.

The specific steps and process features of the homogeneously catalyzed hydrogenation of carbon dioxide to formic acid in the presence of water and methanol are described in PCT/EP 2011/060012.

As homogeneous catalyst, preference is given to using a metal-organic complex comprising an element of group 8, 9 or 10 of the Periodic Table. The complex preferably further comprises at least one phosphine group having at least one unbranched or branched, acyclic or cyclic aliphatic radical having from 1 to 12 carbon atoms, where individual carbon atoms can also be replaced by >P—. The hydrogenation is preferably carried out at from 20 to 200° C. and from 0.2 to 30 MPa abs. The output from the hydrogenation stage (a) is preferably a two-phase mixture. The upper phase comprises tertiary amine (I) and homogeneous catalyst, while the lower phase comprises formic acid, tertiary amine (I), water, methanol and likewise homogeneous catalyst. The two phases are separated and the upper phase comprising tertiary amine (I) and homogeneous catalyst is recirculated to the hydrogenation stage (a). The lower phase comprising formic acid, tertiary amine (I), water, methanol and homogeneous catalyst is preferably extracted with tertiary amine (I) in order to extract the major part of the homogeneous catalyst present therein and recirculate it together with the tertiary amine (I) likewise to the hydrogenation stage (a). The remainder of the lower phase, which comprises formic acid, tertiary amine (I), water and methanol, is then recirculated to step (b) in order then to separate off, as described above, methanol and according to the invention water and organic decomposition products of the tertiary amine (I).

As regards the further work-up, mention may also be made, for the purpose of supplementary information, of the specific steps and process features mentioned in PCT/EP 2011/060012.

In a preferred embodiment of the process of the invention, the tertiary amine (I) to be used in step (a) and the degree of separation in the distillation apparatus mentioned in step (c) are selected so that two liquid phases are formed in the bottom output from the distillation apparatus mentioned in step (c),
(d) the bottom output from the distillation apparatus mentioned in step (c) is separated into two liquid phases, where
the upper liquid phase has a molar ratio of formic acid to tertiary amine (I) of from 0 to 0.5 and the lower liquid phase has a molar ratio of formic acid to tertiary amine (I) of from 0.5 to 5;
(e) the upper liquid phase from the phase separation in step (d) is recirculated to step (a); and
(f) the lower liquid phase from the phase separation in step (d) is recirculated to step (b) and/or (c).

The formation of two liquid phases is determined mainly by the chemical and physical properties of the two phases. These can in turn be influenced by the choice of the tertiary amine (I) to be used, by the degree of separation in the distillation apparatus and also by the presence of any additional components such as solvents and the concentrations thereof.

For the present purposes, the degree of separation is the quotient $$\frac{m_{formic\ acid}(\text{feed stream to step}(c))\,[g/h] - m_{formic\ acid}(\text{bottom output})\,[g/h]}{m_{formic\ acid}(\text{feed stream to step}(c))\,[g/h]} \cdot 100\%$$

where "$m_{formic\ acid}$ (feed stream to step (c))" is the amount of formic acid fed per unit time to the distillation apparatus and "$m_{formic\ acid}$(bottom output)" corresponds to the amount of formic acid discharged per unit time in the bottom output. In this preferred embodiment of the process of the invention, the degree of separation selected is generally ≥10%, preferably ≥25% and particularly preferably ≥40%, and generally ≤99.9%, preferably ≤99.5% and particularly preferably ≤99.0%. The degree of separation can, for example, be easily influenced by the temperature and pressure conditions in the distillation apparatus and by the residence time in the distillation apparatus. It can be determined by means of simple tests, optionally also during operation of the process of the invention.

The suitability of a tertiary amine (I) or a solvent which is optionally additionally desired can be determined, for example, in simple tests in which the number of phases is determined under the conditions envisaged.

The phase separation can, for example, be carried out in a separate phase separator located downstream of the distillation apparatus. However, it is also possible to integrate the phase separator into the bottom region of the distillation apparatus, in the region of the bottom vaporizer or else in the region of the bottom vaporizer circuit. Here, it is also possible or may even be advantageous to use, for example, a centrifugal separator.

Since the formation of two liquid phases is also influenced by the temperature in addition to the chemical and physical properties of the two phases and the miscibility generally increases with temperature, it may be advantageous to operate the phase separation at a lower temperature than the temperature at the bottom previously selected in order to improve the phase separation. For this purpose, the bottom output is usually cooled to a temperature in the range from 30 to 180° C. in an intermediate heat exchanger. The phase separation is preferably carried out at a temperature of ≥50° C. and at a temperature of ≤160° C. and particularly preferably at a temperature of ≤130° C.

The upper liquid phase in step (d) has a molar ratio of formic acid to tertiary amine (I) of generally from 0 to 0.5, preferably ≥0.005 and particularly preferably 0.015, and preferably ≤0.25 and particularly preferably ≤0.125. The lower liquid phase in step (d) has a molar ratio of formic acid to tertiary amine (I) of generally from 0.5 to 4, preferably ≥0.75 and particularly preferably ≥1, and preferably ≤3.5 and particularly preferably ≤3. However, depending on the choice of the amine, it can of course also be possible for the phase comprising formic acid to form the upper phase and the amine phase having a molar formic acid:amine ratio of from 0 to 0.5 to form the lower phase. The only important thing is that phase separation occurs, with one phase having a molar ratio of formic acid to tertiary amine of generally from 0 to 0.5 and a second phase having a molar ratio of formic acid to tertiary amine of generally from 0.5 to 4. The upper phase is preferably that having a molar ratio of formic acid to tertiary amine of generally from 0 to 0.5 and the lower phase is preferably that having a molar ratio of formic acid to tertiary amine of generally from 0.5 to 4.

Furthermore, it is advantageous in the process of the invention to select the degree of separation of the distillation apparatus mentioned in step (c) in such a way that the molar ratio of formic acid to tertiary amine (I) in the bottom output is from 0.1 to 2.0. For the purposes of the present invention, the bottom output is the totality of the liquid bottom condensates which leave the distillation apparatus and are separated into two liquid phases in step (d). It is in consequential whether the bottom condensates originate, for example, directly from the bottom of the distillation apparatus, the bottom of the bottom vaporizer or from both. The degree of separation of the distillation apparatus mentioned in step (c) is preferably selected so that the molar ratio of formic acid to tertiary amine (I) in the bottom output is preferably ≤1.5.

As a result of the preferred recirculation of the upper liquid phase from the phase separation in step (d) to step (a) as per step (e), the tertiary amine (I) comprised in the upper liquid phase can be used, by combination with the formic acid source, for further generation of a stream comprising formic acid and tertiary amine (I). In general, from 10 to 100%, preferably from 50 to 100%, particularly preferably from 80 to 100%, very particularly preferably from 90 to 100% and in particular from 95 to 100%, of the upper liquid phase is recirculated to step (a).

It is of course also possible for further process steps to be integrated into the recirculation of the upper liquid phase. As a nonlimiting example, mention may be made of a purification of the upper liquid phase to be recirculated or of the tertiary amine (I) comprised therein in order to remove undesirable accompanying materials, reaction by-products or further impurities. The type of intermediate process steps are in principle not subject to any limits. It is also possible to remove part of the upper liquid phase in a targeted manner as "purge stream". Missing amounts of tertiary amine (I) or amounts of this which have been lost can naturally be replaced again by fresh tertiary amine (I) which, for example, can be introduced via the recycle stream or directly into step (a).

The preferred recirculation of the lower liquid phase from the phase separation in step (d) to step (b) and/or (c) as per step (f) enables the formic acid comprised in the lower liquid phase likewise to be utilized for isolating formic acid by removal by distillation. Depending on the desired embodiment, the lower liquid phase can thus be recirculated (i) to step (b), (ii) partly to step (b) and partly to (c) or (iii) to step (c). However, preference is generally given to recirculation to step (c) since the stressing of the lower liquid phase comprising formic acid and tertiary amine (I) is usually the lowest in this case and the quantity of the stream in step (b) is not increased, which would otherwise have the consequence of correspondingly larger dimensions. In general, from 10 to 100%, preferably from 50 to 100%, particularly preferably from 80 to 100%, very particularly preferably from 90 to 100% and in particular from 95 to 100%, of the lower liquid phase is recirculated to step (b) and/or (c).

However, it is also possible to recirculate a further part of the lower liquid phase to step (a) in addition to the abovementioned recirculation to step (b) and/or (c). This is, for example, advantageous when the formic acid is produced by transition metal-catalyzed hydrogenation of carbon dioxide, since this is generally carried out in the presence of a polar solvent which likewise accumulates in the lower liquid phase and can thus be recirculated to step (a).

It is of course also possible for further process steps to be integrated into the recirculation of the lower liquid phase. As a nonlimiting example, mention may, here too, be made of a purification of the lower liquid phase to be recirculated or of the tertiary amine (I) comprised therein and/or the formic acid comprised therein in order to remove undesirable accompanying materials, reaction by-products or further impurities. The type of intermediate process steps is also in principle not subject to any limits. It is also possible to discharge part of the lower liquid phase in a targeted manner as "purge stream" in order to remove, for example, undesirable accompanying materials, reaction by-products or further impurities.

The tertiary amine (I) which is preferably to be used in the process of the invention has the general formula (Ia)

$$NR^1R^2R^3 \quad (Ia),$$

where the radicals $R^1$ to $R^3$ are identical or different and are each, independently of one another, an unbranched or branched, acyclic or cyclic, aliphatic, araliphatic or aromatic radical having in each case from 1 to 16 carbon atoms, preferably from 1 to 12 carbon atoms, where individual carbon atoms can also be, independently of one another, replaced by a heterogroup selected from the group consisting of —O— and >N— and two or all three radicals can also be joined to one another to form a chain comprising at least four atoms.

Examples of suitable amines are:
Tri-n-propylamine ($bp_{1013\ hPa}$=156° C.), tri-n-butylamine, tri-n-pentylamine, tri(3-methylbutyl)amine, tri-n-hexylamine, tri-n-heptylamine, tri-n-octylamine, tri-n-nonylamine, tri-n-decylamine, tri-n-undecylamine, tri-n-dodecylamine, tri-n-tridecyl-amine, tri-n-tetradecylamine, tri-n-pentadecylamine, tri-n-hexadecylamine, tri(2-ethylhexyl)amine, tri(2-propylheptyl)amine.
Dimethyldecylamine, dimethyldodecylamine, dimethyltetradecylamine, ethyl-di(2-propyl)amine ($bp_{1013\ hPa}$=127° c.), di-n-octylmethylamine, di-n-hexylmethylamine, di-n-hexyl(2-methylpropyl)amine, di-n-hexyl(3-methylbutyl)amine, methyl-di(2-ethylhexyl)amine, di-n-hexyl(1-methyl-n-hexyl)amine, di-2-propyldecylamine.
Tricyclopentylamine, tricyclohexylamine, tricycloheptylamine, tricyclooctylamine and derivatives thereof substituted by one or more methyl, ethyl, 1-propyl, 2-propyl, 1-butyl, 2-butyl or 2-methyl-2-propyl groups.
Dimethylcyclohexylamine, methyldicyclohexylamine, diethylcyclohexylamine, ethyl-dicyclohexylamine, dimethylcyclopentylamine, methyldicyclopentylamine, methyl-dicyclohexylamine.
Triphenylamine, methyldiphenylamine, ethyldiphenylamine, propyldiphenylamine, butyldiphenylamine, 2-ethylhexyldiphenylamine, dimethylphenylamine, diethyl-phenylamine, dipropylphenylamine, dibutylphenylamine, bis(2-ethylhexyl)phenyl-amine, tribenzylamine, methyldibenzylamine, ethyldibenzylamine and derivatives thereof substituted by one or more methyl, ethyl, 1-propyl, 2-propyl, 1-butyl, 2-butyl or 2-methyl-2-propyl groups.

1,5-Di(1-piperidyl)pentane, N—$C_1$-$C_{12}$-alkylpiperidines, piperazines, N—$C_1$-$C_{12}$-alkylpyrrolidines, N—$C_1$-$C_{12}$-alkylimidazoles and derivatives thereof substituted by one or more methyl, ethyl, 1-propyl, 2-propyl, 1-butyl, 2-butyl or 2-methyl-2-propyl groups.

1,8-Diazabicyclo[5.4.0]undec-7-ene ("DBU"), 1,4-diazabicyclo[2.2.2]octane, N-methyl-8-azabicyclo[3.2.1] octane ("tropane"), N-methyl-9-azabicyclo[3.3.1] nonane ("granatane"), 1-azabicyclo[2.2.2]octane ("quinuclidine"), 7,15-diazatetracyclo-[7.7.1.0$^{2,7}$0.0$^{10,15}$]heptadecane ("sparteine").

It is naturally also possible to use mixtures of various tertiary amines (I) in the process of the invention. Naturally, all tertiary amines (I) used then preferably have, at a pressure of 1013 hPa abs, a boiling point which is at least 5° C. higher than that of formic acid.

Among the above-described tertiary amines of the general formula (Ia), preference is in turn given to those in which the radicals $R^1$ to $R^3$ are identical or different and are each, independently of one another, an unbranched or branched, acyclic or cyclic, aliphatic, araliphatic or aromatic radical having in each case from 1 to 16 carbon atoms, preferably from 1 to 12 carbon atoms, where individual carbon atoms may also be, independently of one another, replaced by a heterogroup selected from the group consisting of —O— and >N— and two or all three radicals can also be joined to one another to form a saturated chain comprising at least four atoms.

Preference is given to at least one of the radicals on the alpha-carbon atom, i.e. on the carbon atom bound directly to the amine nitrogen atom, having two hydrogen atoms.

In the process of the invention, particular preference is given to using an amine of the general formula (Ia) in which the radicals $R^1$ to $R^3$ are selected independently from the group consisting of $C_1$-$C_{12}$-alkyl, $C_5$-$C_8$-cycloalkyl, benzyl and phenyl as tertiary amine (I).

Very particular preference is given to using a saturated amine of the general formula (Ia) as tertiary amine (I) in the process of the invention.

In particular, an amine of the general formula (Ia) in which the radicals $R^1$ to $R^3$ are selected independently from the group consisting of $C_5$-$C_8$-alkyl, in particular tri-n-pentylannine, tri-n-hexylamine, tri-n-heptylamine, tri-n-octylamine, dimethylcyclohexyl-amine, methyldicyclohexylamine, dioctylmethylamine and dimethyldecylamine, is used as tertiary amine (I) in the process of the invention.

In a further embodiment, amines which have a branch on the alpha-carbon atom (the carbon atom bound directly to the amine nitrogen atom), on the beta-carbon atom (the second carbon atom from the amine nitrogen atom) or the gamma-carbon atom (the third carbon atom from the amine nitrogen atom) are used. Here, alkyl, aryl and other substituents are conceivable in principle, with preference being given to alkyl groups such as methyl, ethyl, or 1-propyl or 2-propyl groups or piperidinyl groups. In this embodiment, particular preference is given to N-ethylpiperidine, tri(3-methylbutyl)amine, di-n-hexyl(2-methylpropyl)amine, di-n-hexyl(3-methylbutyl)amine, methyldi(2-ethylhexyl)amine, di-n-hexyl(1-methyl-n-hexyl)amine, di-2-propyldecylamine, methyldicyclohexylamine, 1,5-di(1-piperidyl)pentane.

The streams comprising formic acid and tertiary amine (I) which are formed in the process of the invention can comprise not only free formic acid and the free tertiary amine (I) but also, in admixture with these, formic acid and the tertiary amine (I) in various other forms. The type and amount of the individual forms can differ as a function of the prevailing conditions, for instance the relative ratio of formic acid to tertiary amine (I), the presence of further components (for example water, solvents, by-products, impurities) and thus ultimately also the concentration of formic acid and tertiary amine (I), the temperature and the pressure. Thus, for example, the following conceivable forms may be mentioned:

Ammonium formate (molar ratio of formic acid to tertiary amine (I) of 1) or formic acid-rich adduct with the tertiary amine (I) (molar ratio of formic acid to tertiary amine (I) of >1).

Ionic liquid.

The type and amount of the individual forms is inconsequential for carrying out the process of the invention.

The liquid stream from step (b) to be fed to step (c) can naturally comprise not only formic acid and tertiary amine (I) but also further components such as secondary components and also water and organic decomposition products of the tertiary amine (I) which have not been separated off or not been separated off completely in step (b). Preference is given to feeding only components which can be separated off by distillation without problems from formic acid in step (c) or at least are easy to separate off from the resulting formic acid in a downstream step, for example by means of a subsequent distillation, extraction, absorption or adsorption, to step (c) in addition to formic acid and tertiary amine (I).

The concentration of possible further components apart from formic acid and tertiary amine (I) in the liquid stream to be fed to step (c) or the content of formic acid and tertiary amine (I) in this stream is in principle generally inconsequential for carrying out the process of the invention, as long as the formic acid can be separated off without problems from these in the desired purity. However, in terms of the efficiency of the process of the invention, it is advantageous for formic acid and the tertiary amine (I) not to be fed in an excessively high dilution to step (c) since dilution naturally generally also influences the size and design of the distillation apparatus and its energy consumption. In general, it is therefore advisable to feed in a stream having a total content of formic acid and tertiary amine (I) of at least 10% by weight to 100% by weight, preferably at least 50% by weight and particularly preferably at least 80% by weight.

The liquid stream from step (b) to be fed to step (c) can optionally also comprise solvents.

If a solvent is to be used, it is advantageous, particularly in the preferred variant in which two liquid phases are formed in the bottom output from the distillation apparatus mentioned in step (c), for this to be immiscible or only insignificantly miscible with the tertiary amine (I) but readily miscible with the formic acid-comprising amine phase and therefore tending to be present in the lower liquid phase in step (d). A critical parameter here has been found to be an electrostatic factor, also referred to as EF for short, of preferably 200×10$^{-30}$ Cm, at 25° C. The electrostatic factor EF is defined as the product of the relative dielectric constant $s_r$ and the dipole moment μ of the solvent (see, for example, C. Reichardt, "Solvents and Solvent Effects in Organic Chemistry", 3rd edition, Wiley-VCH Verlag GmbH & Co KGaA, Weinheim 2003, Chapter 3.2, page 67 bottom to page 68 top). This preferred value ensures that the optional solvent has a certain minimum polarity and is miscible with the lower liquid phase in step (d).

The use of solvents can, depending on the respective system (for example type of tertiary amine (I), concentrations, temperature, pressure and the like) improve, for example, the separation of the two liquid phases.

As classes of substances which are particularly suitable as optional solvent, possibilities are, in particular, formic esters, diols and formic esters thereof, polyols and formic esters thereof, sulfones, sulfoxides, open-chain or cyclic amides and also mixtures of the classes of substances mentioned.

Suitable diols and polyols are, for example, ethylene glycol (EF=290.3×10$^{-30}$ Cm), diethylene glycol (EF=244.0×10$^{-30}$ Cm), triethylene glycol, polyethylene glycol, 1,3-propanediol (EF=285.6×10$^{-30}$ Cm), 2-methyl-1,3-propanediol, 1,4-butanediol (EF=262.7×10$^{-30}$ Cm), dipropylene glycol, 1,5-pentanediol (EF=212.5×10$^{-30}$ Cm), 1,6-hexanediol and glycerol. Due to their OH groups, diols and polyols can be esterified in the presence of formic acid. In the process of the invention, this occurs mainly in step (c) during the thermal separation of the stream comprising formic acid and tertiary amine (I) in the distillation apparatus mentioned. Since the formic esters formed display very similar phase behavior, they are generally likewise well suited as solvents. The water formed in the esterification also does no harm in the thermal separation. An accumulation of water in continuous operation of the process of the invention does not occur since water in these small amounts can be separated off via a side offtake on the distillation apparatus.

Suitable sulfoxides are, for example, dialkyl sulfoxides, preferably $C_1$-$C_6$-dialkyl sulfoxides, in particular dimethyl sulfoxide (EF=627.1×10$^{-30}$ Cm).

Suitable open-chain or cyclic amides are, for example, formamide (EF=1243.2×10$^{-30}$ Cm), N-methylformamide (EF=2352.9×10$^{-30}$ Cm), N,N-dimethyl-formamide (EF=396.5×10$^{-30}$ Cm), N-methylpyrrolidone (EF=437.9×10$^{-30}$ Cm), acetamide and N-methylcaprolactam.

However, it may also be advantageous to use a rather nonpolar solvent having an EF of <200×10$^{-30}$ Cm, at 25° C. Nonpolar solvents may be able to reduce the concentration of formic acid in the upper liquid phase.

However, the process of the invention is preferably carried out without addition of a solvent.

FIG. 1 shows a simplified block diagram of a general embodiment of the process of the invention. In the figure, the individual letters have the following meanings:
A=apparatus for producing a stream comprising formic acid, tertiary amine (I) and water
B=apparatus for separating off water, organic decomposition products of the tertiary amine (I) and optionally secondary components
C=distillation apparatus
E=phase separation vessel.

Water and a formic acid source are fed via stream (1) and tertiary amine (I) is fed via stream (8) to the apparatus A for producing a stream comprising formic acid, tertiary amine (I) and water. As indicated above, the formic acid source to be fed in can comprise, for example, formic acid in chemically bound form or a precursor by means of which formic acid is produced by chemical reaction in apparatus A. The stream (2) comprising formic acid, tertiary amine (I) and water is taken off from apparatus A and fed to apparatus B in order to separate off water and organic decomposition products of the tertiary amine (I). This apparatus can be, for example, a distillation apparatus. Water and organic decomposition products of the tertiary amine (I) which have been separated off are taken off via stream (3) and fed to the phase separation vessel E. In this, two liquid phases are formed. The lower, water-comprising liquid phase is recirculated as stream (3x) to the apparatus A. The upper liquid phase enriched in organic decomposition products of the tertiary amine (I) is taken off as stream (3y) and discharged from the process. The stream enriched in formic acid and tertiary amine (I) is fed via stream (4) to the distillation apparatus C. In this, formic acid is separated off as stream (5) by distillation. The bottoms from the distillation apparatus C are taken off as stream (6).

Figure 2:
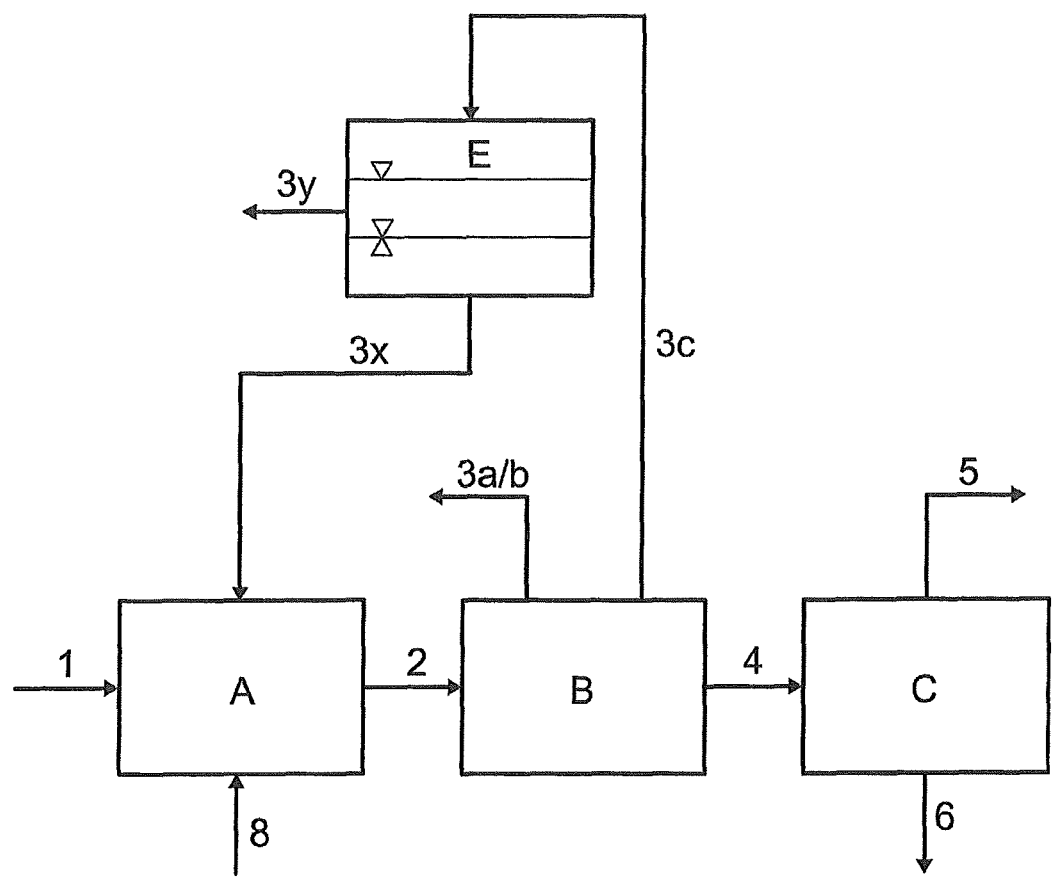
FIG. 2 shows a simplified block diagram of a modified embodiment in which not only water and organic decomposition products of the tertiary amine (I) but also further secondary components are separated off via stream (3a/b) in step (b) of the process of the invention.

FIG. 2 shows a simplified block diagram of a modified embodiment in which not only water and organic decomposition products of the tertiary amine (I) but also further secondary components are separated off via stream (3a/b) in step (b) of the process of the invention. The apparatuses A, B, C and E have the meanings mentioned in the case of FIG. 1. Apparatus B can be, for example, two distillation apparatuses connected in series. However, it is also conceivable for apparatus B to be configured as a single distillation apparatus from which, for example, stream (3a/b) is taken off as overhead stream and stream (3c) is taken off as side stream.

In a variant which is slightly different from FIG. 1, two separate streams are taken off as stream (3a) and (3b) instead of a joint stream (3a/b) from apparatus B.

Figure 3:
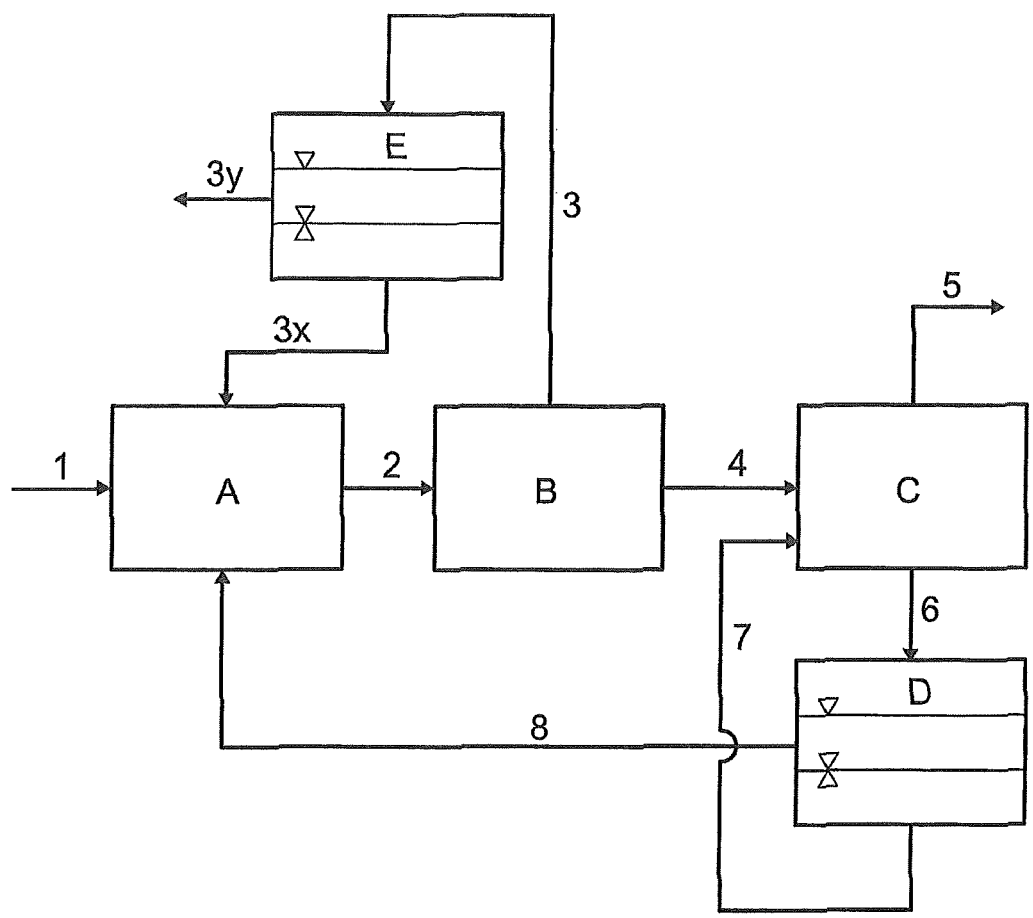
FIG. 3 shows the simplified block diagram of a preferred embodiment with separate recirculation of the bottom output from the distillation apparatus C.

FIG. 3 shows the simplified block diagram of a preferred embodiment with separate recirculation of the bottom output from the distillation apparatus C. The apparatuses A, B, C and E once again have the meanings mentioned in the case of FIG. 1.

Furthermore, FIG. 3 additionally comprises the following apparatuses:
D=phase separation vessel Compared to the simplified block diagram of FIG. 1, in the case of FIG. 3 the bottoms from the distillation apparatus C are fed as stream (6) to the phase separation vessel D and separated into two liquid phases. The upper phase is recirculated as stream (8) to the apparatus A. The lower phase is recirculated as stream (7) to the distillation apparatus C.

In an alternative embodiment, the phase separation vessel D can also be integrated into the distillation apparatus C.

Figure 4:
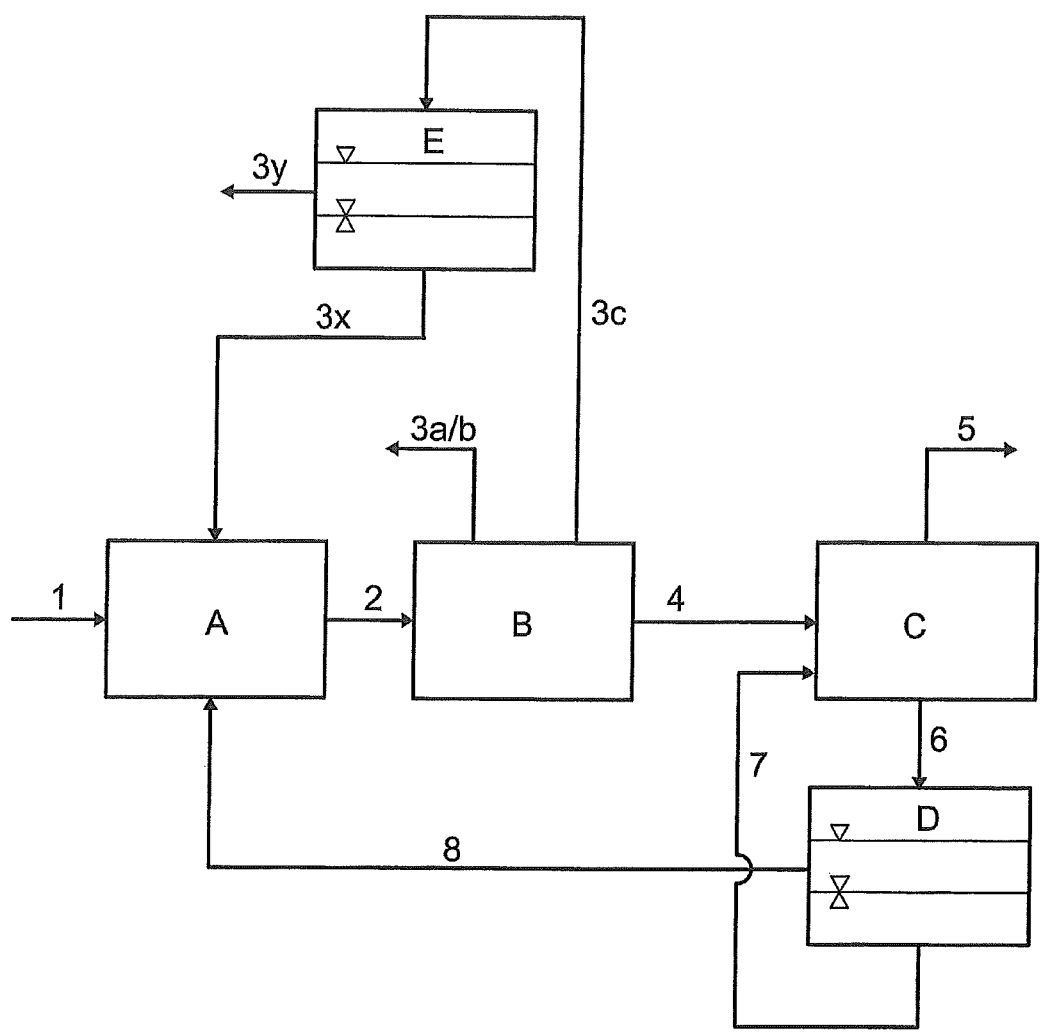
FIG. 4 shows a simplified block diagram of a modified embodiment compared to FIG. 3, in which not only water and organic decomposition products of the tertiary amine (I) but also further secondary components are separated off via stream (3a/b) in step (b) of the process of the invention.

FIG. 4 shows a simplified block diagram of a modified embodiment compared to FIG. 3, in which not only water and organic decomposition products of the tertiary amine (I) but also further secondary components are separated off via stream (3a/b) in step (b) of the process of the invention. As regards the removal of secondary components, reference may also be made to the explanations for FIG. 2.

In the region of the distillation apparatus C and the phase separation D, various embodiments are possible. They differ not only in whether the phase separation is carried out in a separate vessel or integrated into the bottom of the distillation column, but also in the location of the introduction of the stream comprising formic acid and tertiary amine (I) into the distillation apparatus and in the flow between the column vessel and the bottom vaporizer and also the place at which the bottom output is taken off. The embodiments shown in FIGS. 2 to 7 of PCT/EP2011/060,770 and described in the text can also be employed for the purposes of the preferred process according to the invention.

Two preferred embodiments for preferred fields of use of the process of the invention are described below.

Preparation of Formic Acid by Hydrolysis of Methyl Formate

Figure 5:
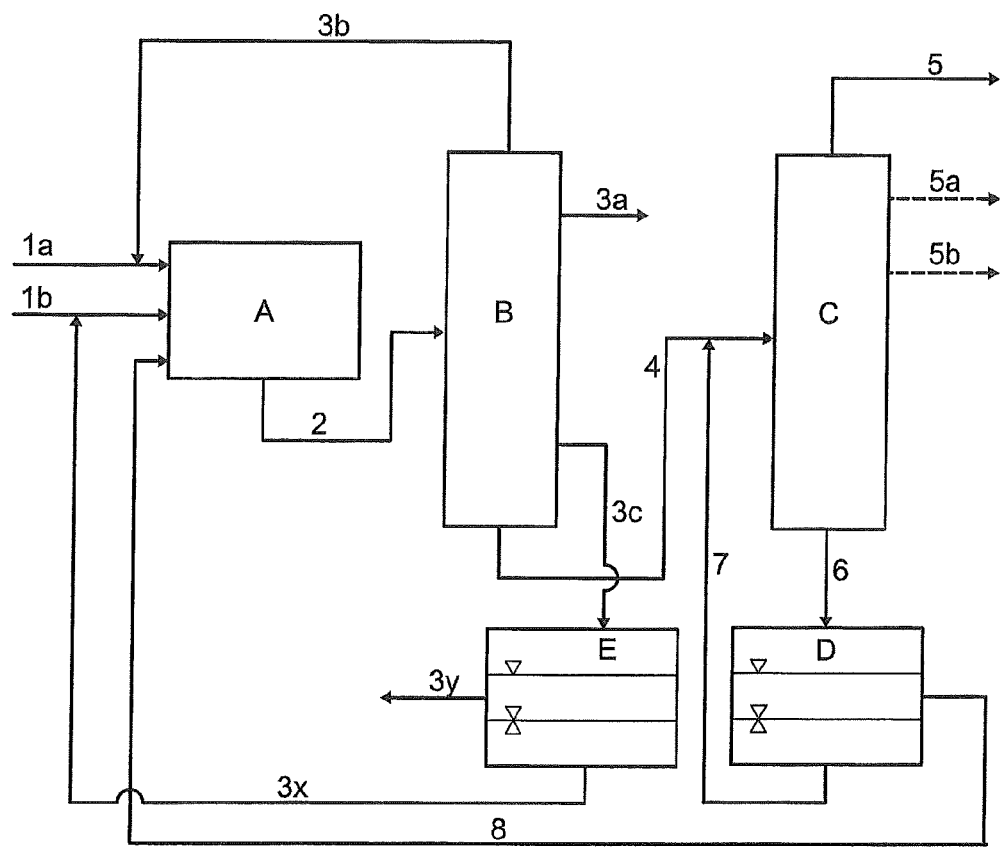
FIG. 5 shows a preferred embodiment for obtaining formic acid by hydrolysis of methyl formate.

A preferred embodiment for obtaining formic acid by hydrolysis of methyl formate is shown in FIG. 5 by means of a simplified block diagram.

In the figure, the individual letters have the following meanings:
A=apparatus for the hydrolysis of methyl formate and production of a stream comprising formic acid, tertiary amine (I) and water
B=distillation apparatus for separating off methyl formate, methanol, water and organic decomposition products of the tertiary amine (I)
C=distillation apparatus for obtaining formic acid
D=phase separation vessel
E=phase separation vessel Methyl formate (streams (1a) and (3b)), water (streams (1b) and (3x)) and tertiary amine (I) (stream (8)) are fed to the apparatus A. A stream comprising formic acid, tertiary amine (1), methanol, water and methyl formate is formed by hydrolysis of methyl formate and is taken off as stream (2) from the apparatus A and fed to the apparatus B. The methyl formate conversion and thus the composition of the stream (2) depends first and foremost on the relative amounts of the three feed streams methyl formate, water and tertiary amine (I) fed to the apparatus A, the type of tertiary amine (I) used, the residence time and the reaction temperature. The conditions appropriate for the respective reaction system can easily be determined by a person skilled in the art, for example by means of preliminary tests. The molar ratio of formic acid to tertiary amine (I) in stream (2) is usually from 0.5 to 5, preferably from 0.5 to 3, with deviations from these ranges naturally also being possible.

In the distillation apparatus B, unreacted methyl formate (stream (3b)), methanol formed in the hydrolysis (stream (3a)) and water and organic decomposition products of the tertiary amine (I) (stream (3c)) are separated off from stream (2). Stream (3b) comprising the unreacted starting material methyl formate is recirculated to the apparatus A. The methanol separated off via stream (3a) can, for example, be reused for preparing methyl formate. Stream (3c) comprising water and organic decomposition products of the tertiary amine (I) is fed to the phase separation vessel E and separated into two liquid phases. The lower phase comprising water is likewise recirculated as stream (3x) to the apparatus A. The upper phase comprising organic decomposition products of the tertiary amine (I) is discharged from the process. Formic acid and tertiary amine (I) are taken off via stream (4). This additionally comprises residual amounts of water. Depending on the way in which the process is carried out, these can amount to a few percent by weight or even some tens of percent by weight of the stream (4). The water content of stream (4) is preferably ≤20% by weight, particularly preferably ≤10% by weight and very particularly preferably ≤5% by weight. The molar ratio of formic acid to tertiary amine (I) is not changed or only insignificantly changed by the distillation apparatus B, so that this ratio is usually also from 0.5 to 5, preferably from 0.5 to 3, in stream (4), with deviations from these ranges naturally also being possible.

Stream (4) is fed to the distillation apparatus C. In this, the formic acid is removed by distillation via stream (5) as overhead product, via stream (5a) as side product and/or via stream (5b) as side product. Depending on the boundary conditions, i.e. especially the composition of the feed stream (4) to the distillation apparatus C and the desired purity of the formic acid, formic acid can be obtained as stream (5) at the top or as stream (5a) as side product in the present embodiment. Water-comprising formic acid is then taken off as side product via stream (5a) or (5b). In some cases, it may even be sufficient to remove formic acid or water-comprising formic acid purely via stream (5) as overhead product. Depending on the specific embodiment, the side stream (5b) or even both side streams (5a) and (5b) can thus be dispensed with. The distillation apparatus C can naturally also have the embodiments disclosed in FIGS. 2 to 7 of PCT/EP2011/060,770.

The bottom product from the distillation apparatus C is fed as stream (6) to the phase separation vessel D. As an alternative, the phase separator D can also be integrated into the distillation apparatus C. The bottom product is separated into two liquid phases in the phase separation vessel D. A heat exchanger, for example, can also optionally be installed between the distillation apparatus C and the phase separation vessel D in order to cool the bottom stream taken off. Although a lower phase separation temperature generally leads to somewhat better separation in respect of the formic acid content, it results in an additional outlay and energy consumption because of the use of a heat exchanger. Advantages and disadvantages therefore have to be weighed against one another in each case. The upper liquid phase from the phase separation vessel D is recirculated via stream (8) to the apparatus A. The lower liquid phase is recirculated via stream (7) to the distillation apparatus C.

Figure 6:
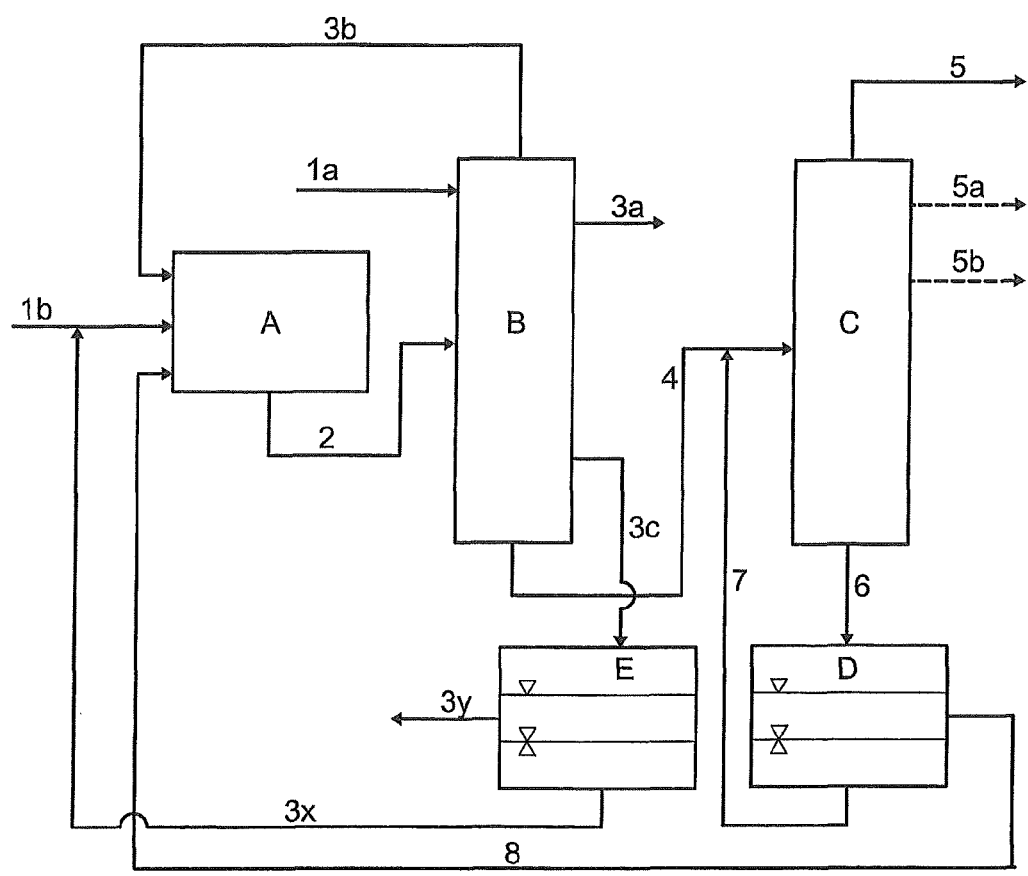
FIG. 6 shows a preferred embodiment for obtaining formic acid by hydrolysis of methyl formate, wherein the methyl formate stream (1a) is introduced into the distillation apparatus B.

In another, preferred embodiment for obtaining formic acid by hydrolysis of methyl formate, the methyl formate stream (1a) is introduced into the distillation apparatus B as shown in FIG. 6. This embodiment is generally advantageous when the methyl formate available as stream (1a) is still contaminated with residual amounts of methanol, for example due to a preceding methyl formate synthesis stage with partial conversion of methanol and incomplete work-up of the methyl formate. As a result of the direct introduction of stream (1a) into the distillation apparatus B, the methanol comprised can be separated off as stream (3a) and, for example, recirculated to the methyl formate synthesis stage. This variant makes it possible to omit a methyl formate/methanol separation entirely in the methyl formate synthesis stage and thus to save an entire distillation column and thus also energy in ongoing operation.

Figure 7:
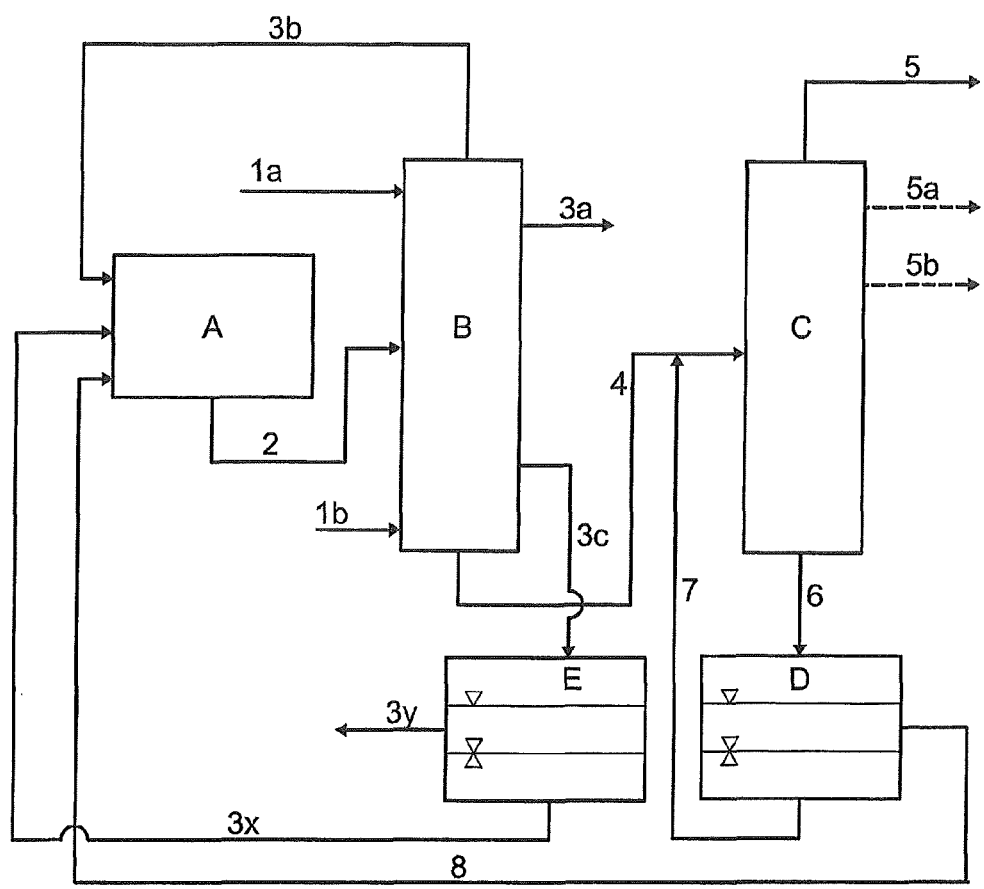
FIG. 7 shows a preferred embodiment for obtaining formic acid by hydrolysis of methyl formate, wherein both the methyl formate stream (1a) and the water stream (1b) are introduced into the distillation apparatus B.

In a further, preferred embodiment for obtaining formic acid by hydrolysis of methyl formate, both the methyl formate stream (1a) and the water stream (1b) are introduced into the distillation apparatus B as shown in FIG. 7. As regards the water stream (1b), this embodiment is generally advantageous when hot condensate or steam is available as water source, since in this way the thermal energy stored therein can be utilized in the distillation apparatus B.

For the sake of completeness, it may be mentioned that, in a further embodiment, it is naturally also possible to introduce the methyl formate stream (1a) into the apparatus A but the water stream (1b) into the distillation apparatus B. This is advantageous when, for example, low-pressure excess steam is available.

Figure 8:
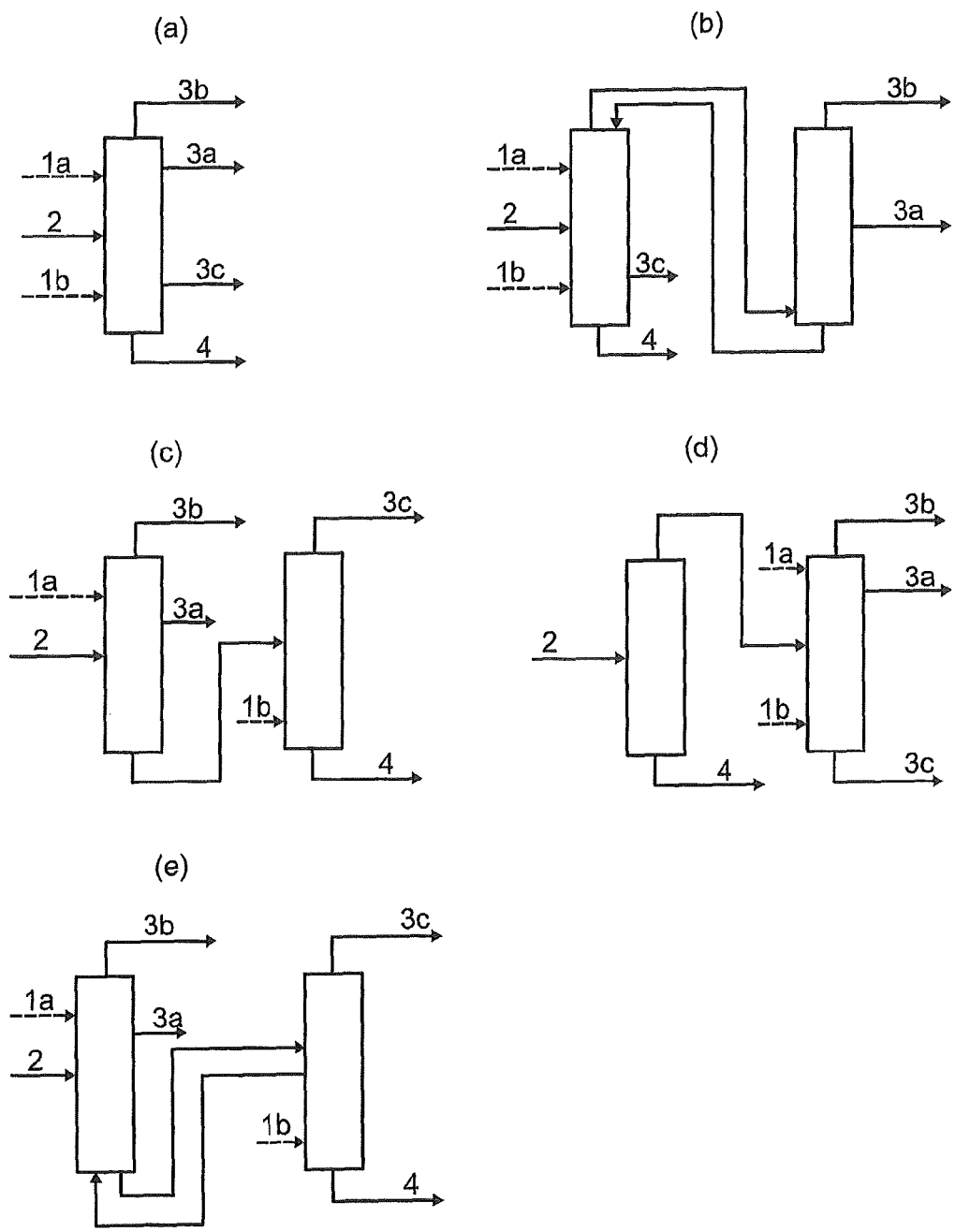
FIG. 8 shows embodiments of the distillation apparatus B having one or two distillation columns.
Figure 9:
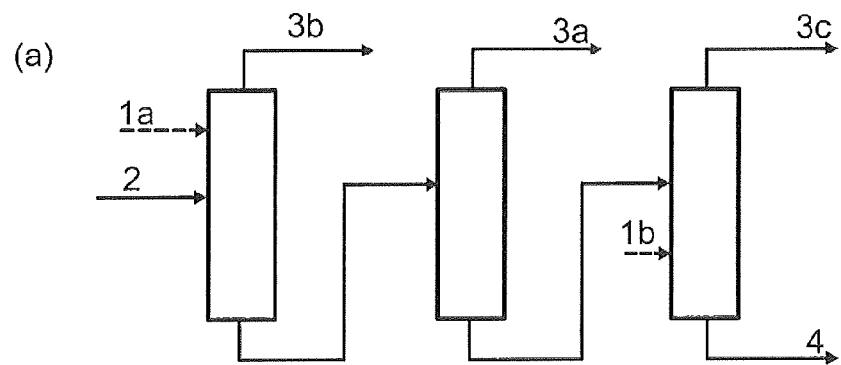
FIG. 9 shows different embodiments of the distillation apparatus B having three distillation columns.
Figure 9:
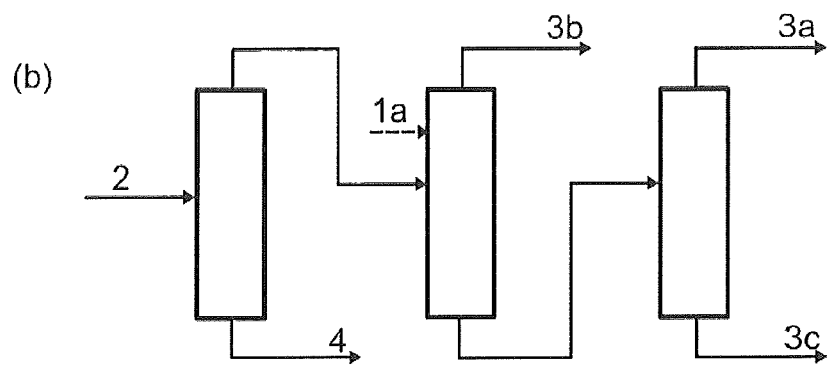
Figure 9:
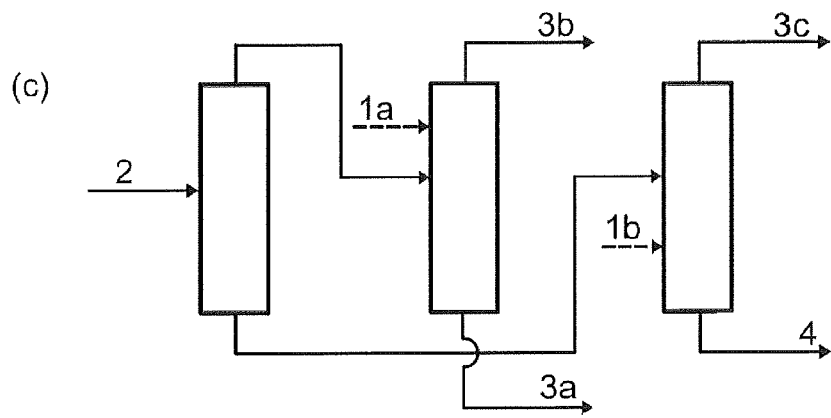

In the variants of FIGS. 5 to 7, specific variants in respect of the embodiment of the distillation apparatus B having one, two or even three distillation columns are possible. FIG. 8a shows an embodiment having one distillation column. FIGS. 8b to 8e show different embodiments having two distillation columns. FIGS. 9a to 9c show different embodiments having three distillation columns. The variants having one or two distillation columns are preferred for the design of the distillation apparatus B. For the sake of completeness, it may be mentioned that, particularly in the embodiments having one or two distillation columns, these can also be configured as thermally coupled columns or a dividing wall column.

Preparation of Formic Acid by Hydrogenation of Carbon Dioxide

Figure 10:
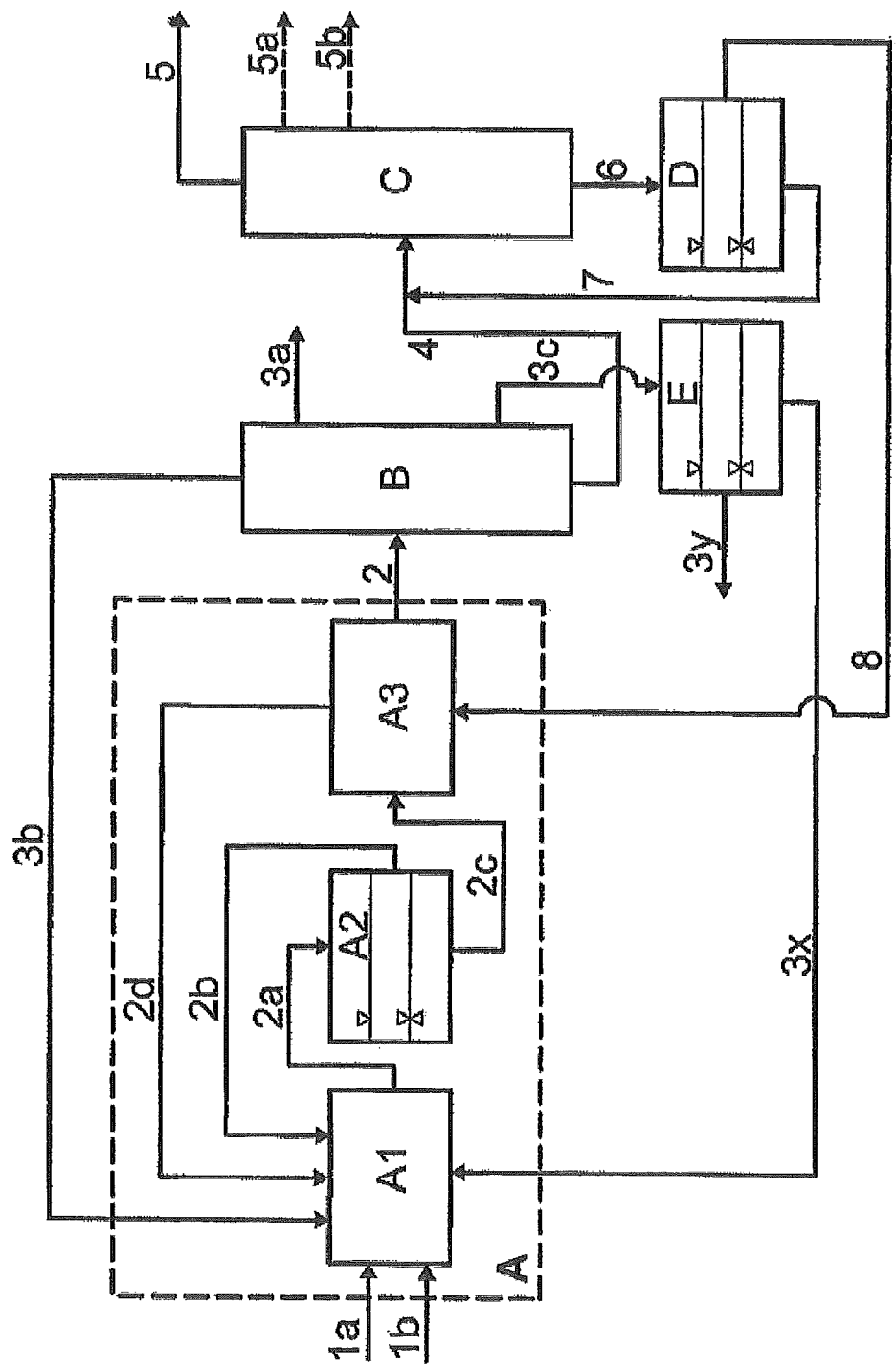
FIG. 10 shows a preferred embodiment for obtaining formic acid by hydrogenation of carbon dioxide.

A preferred embodiment for obtaining formic acid by hydrogenation of carbon dioxide is shown in FIG. 10 by means of a simplified block diagram.

In the figure, the individual letters have the following meanings:
  A=apparatus for the hydrogenation of carbon dioxide and production of a stream comprising formic acid, tertiary amine (I) and water
  A1=hydrogenation reactor
  A2=phase separation vessel
  A3=extraction unit
  B=distillation apparatus for separating off methanol, water and organic decomposition products of the tertiary amine (I)

C=distillation apparatus for obtaining formic acid
D=phase separation vessel
E=phase separation vessel Carbon dioxide (stream (1a)), hydrogen (stream (1b)) and tertiary amine (I) (stream (2d)) are fed to the hydrogenation reactor A1 in the apparatus A. In the hydrogenation reactor A1, the hydrogenation proceeds in the presence of a homogeneous catalyst and of water and methanol as solvent to form a stream (2a) comprising formic acid, tertiary amine (I), methanol, water and homogeneous catalyst. This is fed to the phase separation vessel A2 in which two liquid phases are formed. The upper liquid phase comprising tertiary amine (I) and homogeneous catalyst is recirculated via stream (2b) to the hydrogenation reactor A1. The lower liquid phase comprising formic acid, tertiary amine (I), water, methanol and likewise homogeneous catalyst is conveyed via stream (2c) to the extraction unit A3. In this, the residues of the homogeneous catalyst still present are largely extracted by means of the tertiary amine (I) fed in as stream (8) and are recirculated together with the tertiary amine (I) as stream (2d) to the hydrogenation reactor A1. A stream comprising formic acid, tertiary amine (1) and water is thus obtained as stream (2) and fed to the distillation apparatus B.

Methanol (stream (3b)) and water and organic decomposition products of the tertiary amine (I) (stream (3c)) are separated off from stream (2) in the distillation apparatus B. Stream (3b) comprising methanol is recirculated to the hydrogenation reactor A1 in apparatus A. Stream (3c) comprising water and organic decomposition products of the tertiary amine (I) is fed to the phase separation vessel E and separated into two liquid phases. The lower phase comprising water is likewise recirculated as stream (3x) to the hydrogenation reactor A1 in the apparatus A. The upper phase comprising organic decomposition products of the tertiary amine (I) is discharged from the process. Formic acid and tertiary amine (I) are taken off via stream (4) and conveyed to the distillation apparatus C. With regard to the process steps in respect of the distillation apparatus C and the phase separation vessel D, reference may be made to the above description of the preparation of formic acid by hydrolysis of methyl formate.

The process of the invention makes it possible to obtain formic acid in high yield and high concentration by thermal separation of a stream comprising formic acid and a tertiary amine.

The removal according to the invention of water and organic decomposition products of the tertiary amine (I) with subsequent phase separation of the stream separated off into a water-comprising liquid phase and a liquid phase comprising organic decomposition products of the tertiary amine (I) makes it possible for the process of the invention to be operated very stably with, at the same time, constant high purity of the formic acid produced over long operating times. The formic acid obtained has a low color number and a high color number stability.

The process can be carried out simply, reliably and with a low energy consumption, especially since the surprisingly found possibility of separating off the organic decomposition products of the tertiary amine (I) together with the water and isolating them therefrom by phase separation requires only a very small additional outlay in the form of provision of a suitable phase separation apparatus. As a result of the clever measure according to the invention, neither complicated additional apparatuses nor significant amounts of additional energy are required, in contrast to conventional isolation and discharge of interfering secondary components or decomposition products.

The process of the invention can, in particular, also be used particularly advantageously in conjunction with the hydrolysis of methyl formate as formic acid source and has technical and economic advantages over the production process of methyl formate hydrolysis with subsequent dewatering by means of an extractant or a two-pressure distillation which is at present performed in the industry.

EXAMPLES

Laboratory plant 1 (for Comparative Example 1)

Figure 11:
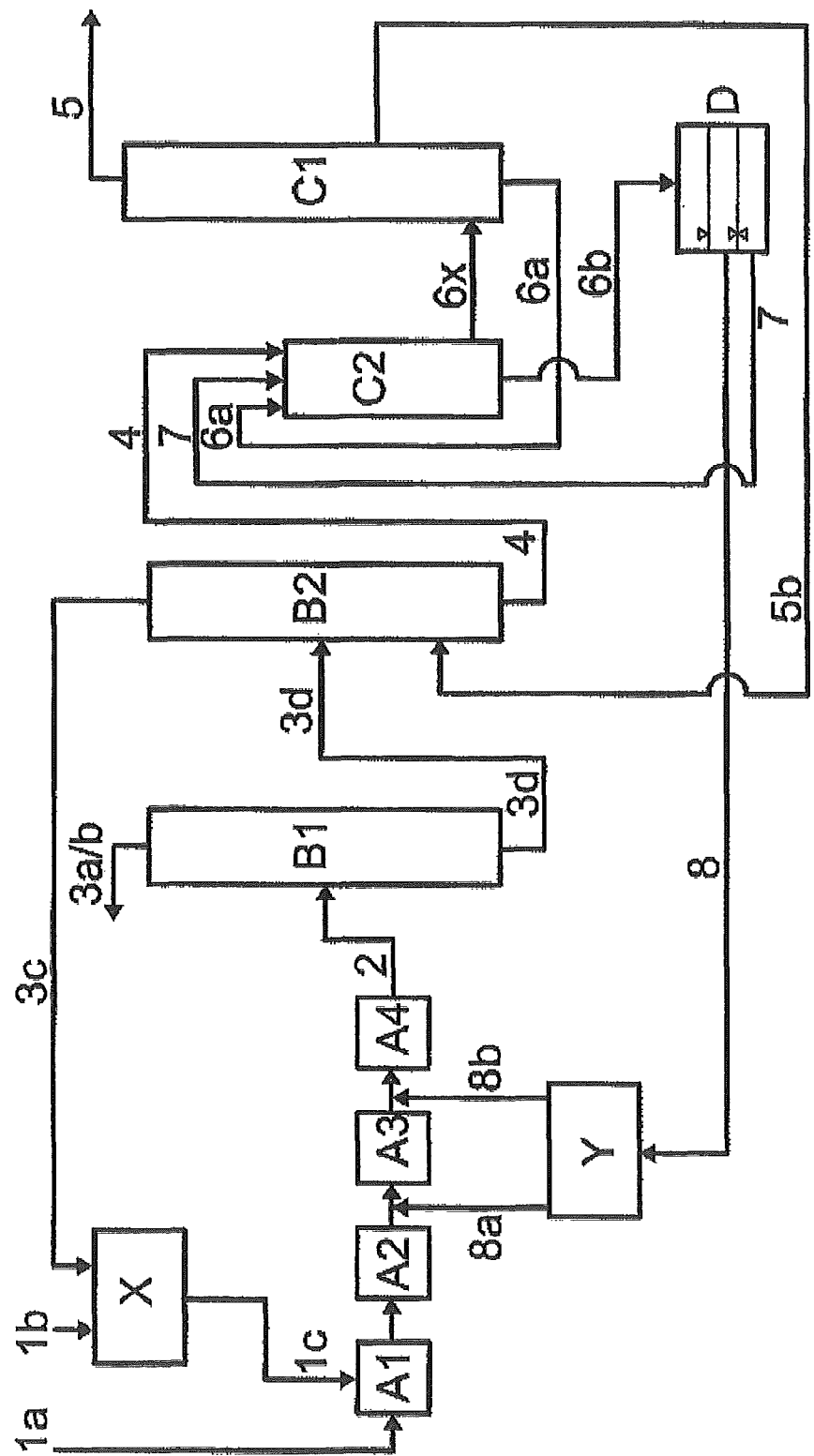
FIG. 11 shows the simplified block diagram of laboratory plant 1.

Laboratory plant 1 serves to examine the continuous process without utilization of the present invention. The simplified block diagram of laboratory plant 1 is shown in FIG. 11. In the figure, the individual letters have the following meanings:

A1=stirred vessel (volume 0.3 l, electrically heated)
A2,3,4=in each case a tube reactor (internal diameter 80 mm, length 1200 mm, filled with 2 mm glass spheres, electrically heated)
X=mixing vessel (volume 5 l)
Y=vessel (volume: 5 l)
B1=distillation apparatus comprising column body (internal diameter 55 mm, provided with two woven mesh packings each having a packing height of 1.3 m and a specific surface area of 750 $m^2/m^3$, with the inlet for stream (2) being located between the two woven mesh packings), oil-heated falling film evaporator and condenser and also regulatable reflux distributor at the top of the column
B2=distillation apparatus comprising column body (internal diameter 55 mm, provided with 12 bubble cap trays in the stripping section and 10 bubble cap trays in the enrichment section, with the inlet for stream (3d) being located between the two parts and the inlet for stream (5b) being located in the stripping section), oil-heated falling film evaporator and condenser and also regulatable reflux distributor at the top of the column
C1=column body (internal diameter 43 mm, provided with a woven mesh packing above the bottom region having a packing height of 0.66 m and a specific surface area of 500 $m^2/m^3$ and a further woven mesh packing having a packing height of 1.82 m and a specific surface area of 750 $m^2/m^3$, with the side offtake for stream (5b) being located between the two woven mesh packings) and condenser and also regulatable reflux distributor at the top of the column
C2=oil-heated falling film evaporator
D=separate phase separation vessel (volume 0.3 l, oil-heated)

The apparatuses and lines comprised a nickel-based alloy having the material number 2.4610. The measurement of the mass flows was carried out by means of a Coriolis flow meter. The laboratory plant 1 was operated continuously.

In all experiments in the laboratory plant 1, the content of formic acid was in each case determined by potentiometric titration with 0.5N NaOH in water and the water content was determined by the Karl Fischer method. All other organic components were in each case determined by gas chromatography.

Laboratory Plant 2 (for Example 2 According to the Invention)

Figure 12:
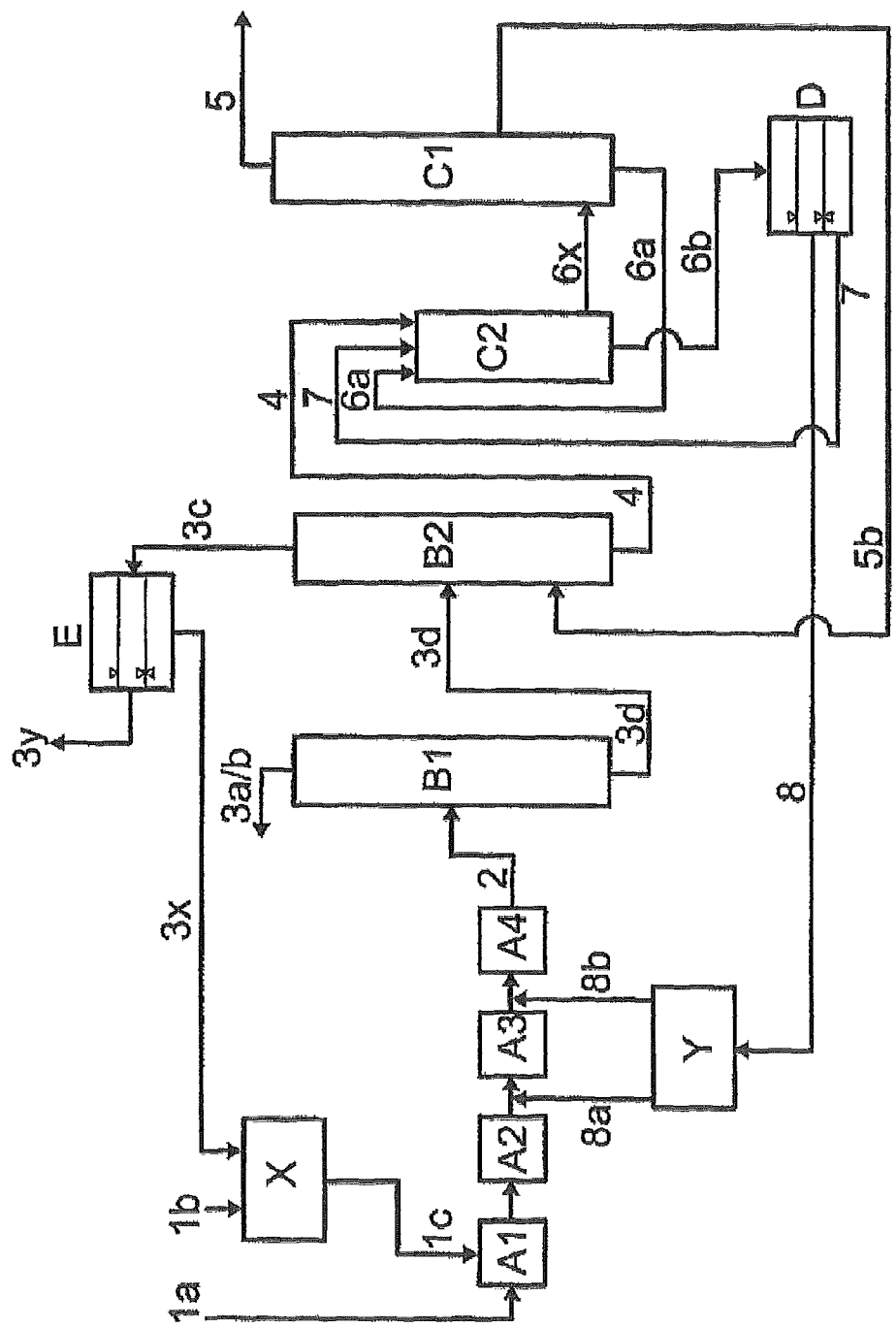
FIG. 12 shows the simplified block diagram of laboratory plant 2.

Laboratory plant 2 is laboratory plant 1 supplemented by a separate phase separation vessel for stream (3c) and served to examine the continuous process utilizing the present invention. The simplified block diagram of laboratory plant 2 is shown in FIG. 12. In the figure, the extra letter has the following meaning:

E=separate phase separation vessel (volume 25 ml, oil-heated)

Otherwise, reference is made to the description of laboratory plant 1.

Example 1

Comparative Example

Example 1 was carried out in laboratory plant 1. 1760 g/h of methyl formate via stream (1a) and 849 g/h of water via stream (1c) were metered by means of metering pumps into the stirred vessel A1. Stream (1c) was taken from the mixing vessel X and was composed of fresh water via stream (1b) and recycled water from the distillation apparatus B2 via stream (3c). Stream (1b) was selected so that the sum of stream (1b) and stream (3c) gave the desired stream (1c). The stirred vessel A1 was operated at 110° C. and 1.3 MPa abs. The output was introduced into tube reactor A2 which was likewise operated at 110° C. and 1.3 MPa abs. The output from tube reactor A2 was introduced into tube reactor A3. 1964 g/h of tri-n-hexylamine were fed via stream (8a) into this tube reactor A3. The output from tube reactor A3 was introduced into tube reactor A4. A further 1661 g/h of tri-n-hexylamine were fed via stream (8b) into this tube reactor A4. The streams (8a) and (8b) were taken from the vessel Y which served to distribute the tri-n-hexylamine recirculated via stream (8) to the two tube reactors A3 and A4. Tube reactor A3 was operated at 115° C. and 1.3 MPa abs, and tube reactor A4 was operated at 110° C. and 1.3 MPa abs. A product mixture comprising 58.4% by weight of tri-n-hexylamine, 16.4% by weight of formic acid, 12.3% by weight of methanol, 7.8% by weight of water and 6.9% by weight of methyl formate was obtained as stream (2).

Stream (2) was depressurized and introduced into the column body of the distillation apparatus B1. At a pressure at the top of 0.18 MPa abs and a reflux ratio of 2.5, a mixture comprising methanol formed and unreacted methyl formate was taken off as overhead product stream (3ab). As bottom product, 5012 g/h of a mixture comprising 71.2% by weight of tri-n-hexylamine, 9.1% by weight of water, 20.7% by weight of formic acid and 0.1% by weight of methanol was obtained as stream (3d). The temperature at the bottom of B1 was 117° C.

Stream (3d) was introduced into the column body of the distillation apparatus B2. In addition, 277 g/h of the side offtake from the column body of distillation apparatus C1, which comprised 79.3% by weight of formic acid and 16.6% by weight of water, was additionally fed in via stream (5b). 450 g/h of stream (3c) were taken off as overhead product from the distillation apparatus B2 at a pressure at the top of 0.10 MPa abs and a reflux ratio of 0.71. Stream (3c), which comprised 98.8% by weight of water and 0.3% by weight of formic acid, was fed to the mixing vessel X for recirculation to the stirred vessel A1.

4821 g/h of a mixture comprising 75.3% by weight of tri-n-hexylamine, 26.0% by weight of formic acid and 1.2% by weight of water were obtained via stream (4) as bottom product at a temperature at the bottom of B2 of 160° C. and were introduced from the top into the evaporator C2. The evaporator C2 and the column body C1 were operated under reduced pressure. The temperature at the lower outlet from the evaporator C2 was 161° C. The gaseous output from the evaporator was fed as stream (6x) to the column body C1. This was operated at a pressure at the top of 0.015 MPa abs and a reflux ratio of runback to distillate of 4.907 g/h of 99.6% strength by weight formic acid were obtained as stream (5) as overhead product of C1. The n-hexyl formate content was <10 ppm by weight and the n-hexanal content was <15 ppm by weight. 277 g/h were taken off as stream (5b) as side offtake and recirculated to the column body B2. The liquid output from the column body C1 was fed as stream (6a) into the top of the evaporator C2.

The liquid output from the evaporator C2 was conveyed as stream (6b) to the phase separation vessel D. This was operated at atmospheric pressure and a temperature of 80° C. Two liquid phases were formed. The upper liquid phase was continuously taken off as stream (8) in an amount of 3587 g/h and introduced into the vessel Y. Stream (8) comprised 95.7% by weight of tri-n-hexylamine and 1.2% by weight of formic acid. The lower liquid phase was conveyed continuously as stream (7) to the evaporator C2. The remaining stream was fed into the top of the evaporator C2.

Figure 13:
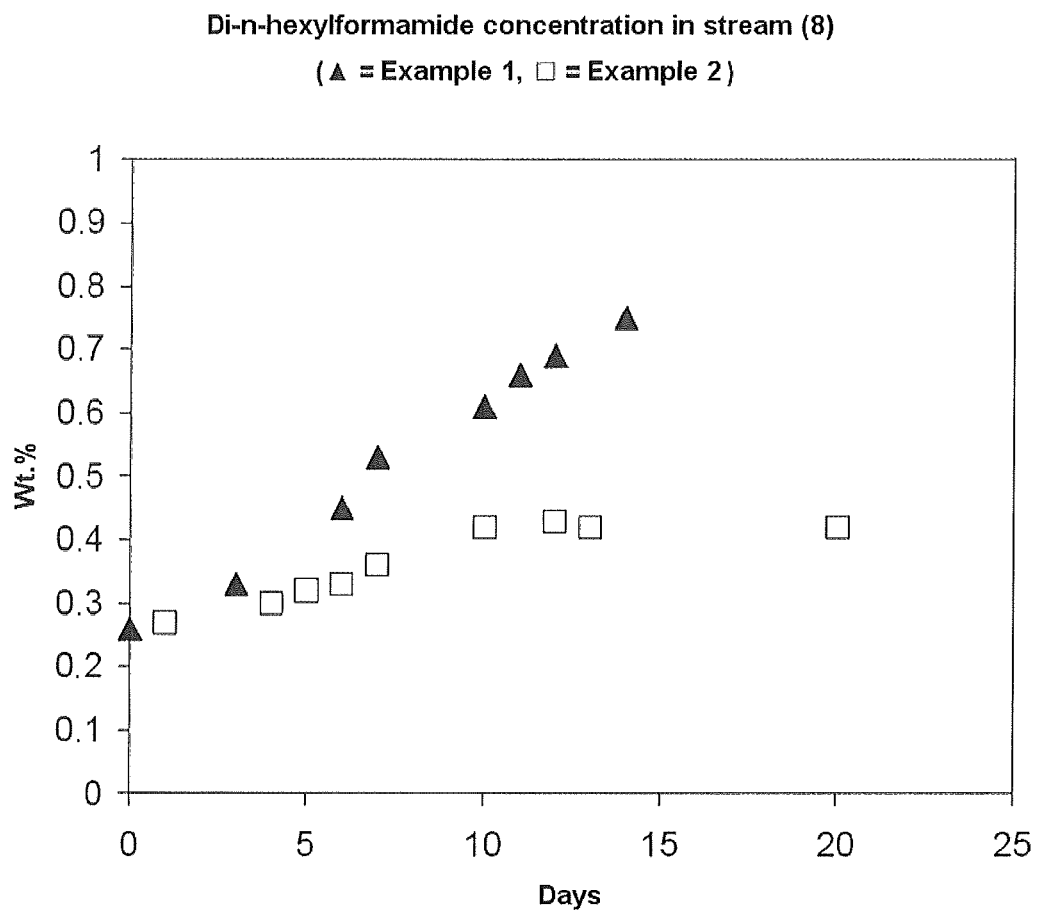
FIG. 13 shows the di-n-hexylformamide concentration of Example 1 in graph form.

In order to ensure the abovementioned operating state, the plant was firstly run in for seven days. During this time, the di-n-hexylformamide concentration in stream (8) rose to 0.26% by weight and continued to rise steadily in the following days. 14 days after start-up, the concentration was already 0.75% by weight. An end to the rise could not be discerned. The di-n-hexylformamide concentration is shown in tabular form in table 1 and in graph form in FIG. 13.

Example 2

Example According to the Invention

Laboratory plant 1 was now converted into laboratory plant 2 and in the process supplemented by the separate phase separation vessel E. The plant was started up again and stable operating parameters were again reached within seven days. Except for the region around the phase separation vessel E, these correspond to the values given in example 1.

However, unlike example 1, the stream (3c) amounting to 450 g/h taken off as overhead product from the distillation apparatus B2 was fed to the phase separation vessel E which was operated at 30° C. Stream (3x) was taken off therefrom at the bottom and fed to the mixing vessel X for recirculation to the stirred vessel A1. Stream (3x) comprised 99.3% by weight of water and 0.15% by weight of formic acid. Some days after start-up of the plant, a further, upper phase was slowly formed. This was then removed daily as stream (3y) and collected. After 13 days (counted from start-up of the plant), a total of 2.4 g of this upper phase had been obtained. It comprised 75.8% by weight of di-n-hexylformamide, 0.3% by weight of tri-n-hexylamine, 0.8% by weight of water, 1.2% by weight of formic acid, 1.1% by weight of n-hexyl formate, 0.1% by weight of n-hexanol and 0.2% by weight of n-hexanal. In addition, 8.8% by area of $C_{1-2}$ aldol condensation products of hexanal were detected in the gas chromatogram.

Eight days after start-up, the di-n-hexylformamide concentration in stream (8) was 0.27% by weight. Over the course of the next ten days, the concentration firstly increased continuously, but then reached a saturation value of 0.42% by weight.

The results from examples 1 and 2 are summarized in table 1, where the time scale commences on the seventh day of running in.

Example 1 demonstrates that without utilization of the measure according to the invention for the targeted removal and discharge of organic degradation products of the tertiary amine (I), in the present example especially di-n-hexylformamide, the concentration of these in stream (8) increases continuously. In addition, example 1 is also evidence of the fact that di-n-hexylformamide is also formed under real operating conditions. Serious problems in long-term operation of such a process would be inevitable.

In contrast thereto, example 2 shows that di-n-hexylformamide and also various other degradation products of the tertiary amine (I) used separate out as upper phase in the phase separation vessel E after only a short period of operation of only a few days and can be removed in a targeted manner. The di-n-hexylformamide concentration in stream (8) can in this way be kept at a low, constant value. Disadvantages such as slowly increasing contamination of the formic acid separated off as desired product in stream (5) and an adverse effect on the phase separation of the bottom product from the distillation apparatus C1/C2 are thus reliably avoided.

Example 3a

Decomposition of Tri-n-Hexylamine in the Presence of Formic Acid and Water 95.3 g (0.35 mol) of tri-n-hexylamine, 16.3 g (0.35 mol) of formic acid (98-100% by weight) and 6.3 g (0.35 mol) of water were mixed in an ice bath in the laboratory. The solution obtained was subsequently warmed to room temperature (about 20° C.) and degassed by evacuation (2 hPa abs) and admission of pure nitrogen, carried out a total of three times. A two-phase solution was obtained. This was then transferred under an $N_2$ atmosphere in a glove box into a 270 ml autoclave (material: HC) and the autoclave was closed. The autoclave was subsequently pressurized with nitrogen to 1.0 MPa abs and heated to 160° C. while stirring vigorously. After the temperature had been reached, a total pressure of 2.5 MPa abs was set by injection of further $N_2$. The reaction mixture was then stirred at 160° C. for 24 hours. The autoclave was subsequently cooled to room temperature, depressurized to atmospheric pressure and the contents were transferred to a glass vessel. The output separated into two phases. 42.1 g of upper phase and 68.4 g of lower phase were obtained. Both phases were analyzed by gas chromatography to determine their di-n-hexylformamide content. The upper phase comprised 0.10% by weight of di-n-hexylformamide, and the lower phase comprised 0.46% by weight of di-n-hexylformamide.

Example 3b

Decomposition of Tri-n-Hexylamine in the Presence of Formic Acid and Water 95.3 g (0.35 mol) of tri-n-hexylamine, 16.3 g (0.35 mol) of formic acid (98-100% by weight) and 6.3 g (0.35 mol) of water were mixed in an ice bath in the laboratory. The solution obtained was subsequently warmed to room temperature (about 20° C.) and degassed by evacuation (2 hPa abs) and admission of pure nitrogen, carried out a total of three times. A two-phase solution was obtained. This was then transferred under an $N_2$ atmosphere in a glove box into a 270 ml autoclave (material: HC) and the autoclave was closed. The autoclave was subsequently pressurized with nitrogen to 1.0 MPa abs and heated to 160° C. while stirring vigorously. After the temperature had been reached, a total pressure of 2.5 MPa abs was set by injection of further $N_2$. The reaction mixture was then stirred at 160° C. for 72 hours. The autoclave was subsequently cooled to room temperature, depressurized to atmospheric pressure and the contents were transferred to a glass vessel. The output separated into two phases. 48.1 g of upper phase and 57.9 g of lower phase were obtained. Both phases were analyzed by gas chromatography to determine their di-n-hexylformamide content. The upper phase comprised 0.16% by weight of di-n-hexylformamide, and the lower phase comprised 0.69% by weight of di-n-hexylformamide.

Examples 3a and 3b show that tri-n-hexylamine decomposes into di-n-hexylformamide at elevated temperature and elevated pressure in the presence of formic acid and water.

Example 4

Decomposition of Tri-n-Hexylamine in the Presence of Oxygen 134.6 g (0.50 mol) of tri-n-hexylamine and 46.5 g (1.0 mol) of formic acid (98-100% by weight) were mixed in a round-bottom flask in an ice bath in the laboratory. The solution obtained was then warmed to room temperature (about 20° C.). The round-bottom flask was then provided with a reflux condenser and the solution was heated to 110° C. while stirring. The reflux condenser was left open at the top so that the solution was continuously in contact with air. The solution was stirred for 66 hours under these conditions and subsequently cooled to room temperature. The output was analyzed by gas chromatography. 1.7% by weight of di-n-hexylformamide and 0.43% by weight of n-hexanal were found therein.

Example 4 demonstrates that tri-n-hexylamine decomposes into di-n-hexylformamide and n-hexanal in formic acid solution in the presence of atmospheric oxygen.

Examples 5 to 7

Influence of Di-n-Hexylformamide on the Phase Separation of a Mixture of Formic Acid and tri-n-hexylamine Example 5

In Example 5, 243.8 g (0.9 mol) of tri-n-hexylamine were placed in a glass flask stirred by means of a magnetic stirrer and 41.8 g (0.9 mol) of formic acid (98-100% by weight) were added dropwise while cooling in an ice bath. After the addition was complete, the solution was warmed to room temperature (about 20° C.) and subsequently heated to 80° C. and stirred at this temperature for 30 minutes. Two phases were obtained. A sample was taken from each phase at 80° C. and analyzed to determine the formic acid content by titration with 0.1 N NaOH in isopropanol with potentiometric end point determination. The tri-n-hexylamine content was in each case assumed to be the balance to 100%.

Analytical data (composition at 80° C.):

|  | Upper phase | Lower phase |
|---|---|---|
| Formic acid | 1.0% by weight | 20.5% by weight |
| Tri-n-hexylamine | 99.0% by weight | 79.5% by weight |

Example 6

In Example 6, 243.8 g (0.9 mol) of tri-n-hexylamine and 17.1 g of di-n-hexylformamide were placed in a glass flask stirred by means of a magnetic stirrer and 17.1 g (0.37 mol) of formic acid (98-100% by weight) were then added dropwise while cooling in an ice bath. After the addition was complete, the solution was warmed to room temperature (about 20° C.) and subsequently heated to 80° C. and stirred at this temperature for 30 minutes. Two phases were likewise obtained. A sample was taken from each phase at 80° C. and analyzed to determine the formic acid content by titration with 0.1 N NaOH in isopropanol with potentiometric end point determination. The contents of di-n-hexylformamide and tri-n-hexylamine were determined by means of a calibrated gas chromatograph.

Analytical data (composition at 80° C.):

|  | Upper phase | Lower phase |
| --- | --- | --- |
| Formic acid | 2.9% by weight | 15.6% by weight |
| Di-n-hexylformamide | 4.6% by weight | 5.9% by weight |
| Tri-n-hexylamine | 92.1% by weight | 78.0% by weight |

Example 7

In Example 7, 243.8 g (0.9 mol) of tri-n-hexylamine and 28.5 g of di-n-hexylformamide were placed in a glass flask stirred by means of a magnetic stirrer and 41.8 g (0.9 mol) of formic acid (98-100% by weight) were then added dropwise while cooling in an ice bath. After the addition was complete, the solution was warmed to room temperature (about 20° C.) and subsequently heated to 80° C. and stirred at this temperature for 30 minutes. In contrast to Examples 5 and 6, only a single phase was obtained here. Analysis of the composition was therefore superfluous.

Examples 5, 6 and 7 demonstrate that phase separation in the system tri-n-hexylamine and formic acid is adversely affected by di-n-hexylformamide. In Example 5 without addition of di-n-hexylformamide, the upper phase comprised only 1.0% by weight of formic acid. The remainder was tri-n-hexylamine. Example 6 shows that even when phase separation is still obtained, the formic acid concentration in the upper phase increases to 2.9% by weight, i.e. more than twice the value in Example 5, as a result of the phase-compatibilizing effect of di-n-hexylformamide, even though the amount of formic acid added in Example 6 was deliberately less than in Example 5. In a continuously operated process for preparing formic acid, in which the bottom output from the pure formic acid column (see distillation apparatus C1/C2 in laboratory plant 1) separates into two phases and these are recirculated separately, a poorer phase separation would inevitably increase the recycle streams unnecessarily. If the amount of di-n-hexylformamide is increased further as in Example 7, phase separation finally does not occur at all.

Examples 8 to 9

Phase Separation of Di-n-Hexylformamide and Water

Example 8

In Example 8, 6.0 g of di-n-hexylformamide and 6.0 g of water were introduced dropwise into a glass flask stirred by means of a magnetic stirrer while cooling in an ice bath. After the addition was complete, the solution was warmed to room temperature (about 20° C.) and subsequently stirred for 30 minutes. Two phases were obtained and these were separated in a phase separation vessel and weighed. A sample was taken from each phase at 25° C. 5.8 g of upper phase and 5.5 g of lower phase were obtained. The water content of the two phases was determined by Karl-Fischer titration with potentiometric end point determination. The di-n-hexylformamide content was in each case assumed to be the balance to 100%.

Analytical data (composition at 25° C.):

|  | Upper phase | Lower phase |
| --- | --- | --- |
| Water | 2.9% by weight | 99.9% by weight |
| Di-n-hexylformamide | 97.1% by weight | 0.1% by weight |

Example 9

In Example 9, 18.4 g of di-n-hexylformamide and 18.4 g of water were introduced dropwise into a glass flask stirred by means of a magnetic stirrer while cooling in an ice bath. After the addition was complete, the solution was firstly warmed to room temperature (about 20° C.) and subsequently heated further to 100° C. and stirred at 100° C. under reflux for 30 minutes. Two phases were also obtained at 100° C. The water content of the two phases was likewise determined by Karl-Fischer titration with potentiometric end point determination. The di-n-hexylformamide content was in each case assumed to be the balance to 100%.

Analytical data (composition at 100° C.):

|  | Upper phase | Lower phase |
| --- | --- | --- |
| Water | 4.3% by weight | 99.9% by weight |
| Di-n-hexylformamide | 95.7% by weight | 0.1% by weight |

Examples 8 and 9 demonstrate that the system di-n-hexylformamide and water has a miscibility gap both at room temperature and at elevated temperature.

Example 10

Decomposition of Tri-n-Pentylamine in the Presence of Formic Acid and Water 81.2 g (0.35 mol) of tri-n-pentylamine, 16.27 g (0.35 mol) of formic acid (98-100% by weight) and 6.31 g of water were mixed in an ice bath in the laboratory. The solution obtained was subsequently warmed to room temperature (about 20° C.) and degassed by evacuation (2 hPa abs) and admission of pure nitrogen, carried out a total of three times. A two-phase solution was obtained. This was then transferred under an $N_2$ atmosphere in a glove box into a 270 ml autoclave (material: HC) and the autoclave was closed. The autoclave was subsequently pressurized with nitrogen to 1.0 MPa and heated to 160° C. while stirring vigorously. After the temperature had been reached, a total pressure of 2.5 MPa abs was set by injection of further $N_2$. The reaction mixture was then stirred at 160° C. for 24 hours. The autoclave was subsequently cooled to room temperature, depressurized to atmospheric pressure and the contents were transferred to a glass vessel. The output separated into two phases. 36.8 g of upper phase and 59.3 g of lower phase were obtained. Both phases were analyzed by gas chromatography to determine their di-n-pentylformamide content. The upper phase comprised 0.15% by weight, and the lower phase comprised 0.45% by weight.

Example 11

Decomposition of Tri-n-Octylamine in the Presence of Formic Acid and Water 123.6 g (0.35 mol) of tri-n-octylamine, 16.3 g (0.35 mol) of formic acid (98-100% by weight) and 6.3 g of water were mixed in an ice bath in the laboratory. The solution obtained was subsequently warmed to room temperature (about 20° C.) and degassed by evacuation (2 hPa abs) and admission of pure nitrogen, carried out a total of three times. A two-phase solution was obtained. This was then transferred under an $N_2$ atmosphere in a glove box into a 270 ml autoclave (material: HC) and the autoclave was closed. The autoclave was subsequently pressurized with nitrogen to 1.0 MPa and heated to 160° C. while stirring vigorously. After the temperature had been reached, a total pressure of 2.5 MPa abs was set by injection of further $N_2$. The reaction mixture was then stirred at 160° C. for 24 hours. The autoclave was subsequently cooled to room temperature, depressurized to atmospheric pressure and the contents were transferred to a glass vessel. The output separated into two phases. 138.2 g of organic upper phase and an aqueous lower phase of 1.3 g were obtained. Both phases were analyzed by gas chromatography to determine their di-n-octylformamide content. The upper phase comprised 0.32% by weight, and the lower phase comprised <0.1% by weight.

The invention claimed is:

1. A process for obtaining formic acid by thermal separation of a stream comprising formic acid and a tertiary amine (I) which at a pressure of 1013 hPa abs has a boiling point which is at least 5° C. higher than that of formic acid, which comprises
    (a) producing a liquid stream comprising formic acid, tertiary amine (I) and water and having a molar ratio of formic acid to tertiary amine (I) of from 0.5 to 5 by combining tertiary amine (I) and a formic acid source in the presence of water;
    (b) separating off water and organic decomposition products of the tertiary amine (I) from the liquid stream obtained from step (a), wherein the organic decomposition products of the tertiary amine (I) are comprised in the tertiary amine (I) fed to step (a) and/or formed during the process up to step (b), thereby the liquid stream is depleted in water and organic decomposition products of the tertiary amine (I); and
    (c) removing formic acid by distillation from the liquid stream comprising formic acid and tertiary amine (I) obtained from step (b) in a distillation apparatus at a temperature at the bottom of from 100 to 300° C. and a pressure of from 30 to 3000 hPa abs;
wherein
    (b1) the stream comprising water and organic decomposition products of the tertiary amine (I) which has been separated off in step (b) is separated into two liquid phases;
    (b2) the upper liquid phase enriched in organic decomposition products of the tertiary amine (I) is removed; and
    (b3) the lower, water-comprising liquid phase is recirculated to step (a),
wherein the tertiary amine (I) is an amine of the general formula (Ia),

$NR^1R^2R^3$  (Ia), wherein the radicals $R^1$ to $R^3$ are identical or different and are each, independently of one another, a radical having in each case from 1 to 16 carbon atoms and wherein the radical is an unbranched or branched, acyclic or cyclic, aliphatic, araliphatic, or aromatic radical, and wherein individual carbon atoms are optionally, independently of one another, replaced by a heterogroup selected from the group consisting of —O— and >N—, and two or all three radicals are optionally joined to one another to form a chain comprising at least four atoms.

2. The process of claim 1, wherein the separation in step (b) is carried out by distillation.

3. The process of claim 1, wherein
    (i) a formic acid source comprising methyl formate is used and a liquid stream comprising formic acid, tertiary amine (I), water and methanol is obtained therefrom by hydrolysis of methyl formate in step (a); and
    (ii) a further stream comprising the methanol formed by dissociation of methyl formate is separated off from the stream obtained from step (a) in step (b).

4. The process of claim 3, wherein
    (i) a further stream comprising unreacted methyl formate is separated off in step (b) from the stream obtained from step (a); and
    (ii) the methyl formate which has been separated off is recirculated to step (a).

5. The process of claim 1, wherein
    (i) a formic acid source which comprises carbon dioxide, hydrogen and a homogeneous catalyst is used in the presence of methanol in step (a) and a liquid stream comprising formic acid, tertiary amine (I), water, and methanol is obtained therefrom by homogeneously catalyzed hydrogenation of carbon dioxide; and
    (ii) a further stream comprising methanol is separated off in step (b) from the stream obtained from step (a), and the methanol which has been separated off is recirculated to step (a).

6. The process of claim 1, wherein the tertiary amine (I) to be used in step (a) and the degree of separation in the distillation apparatus of step (c) are selected so that two liquid phases are formed in the bottom output from the distillation apparatus of step (c), which further comprises
    (d) separating the bottom output from the distillation apparatus of step (c) into two liquid phases, where the upper liquid phase has a molar ratio of formic acid to tertiary amine (I) of from 0 to 0.5 and the lower liquid phase has a molar ratio of formic acid to tertiary amine (I) of from 0.5 to 4;
    (e) recirculating the upper liquid phase from the phase separation in step (d) to step (a); and
    (f) recirculating the lower liquid phase from the phase separation in step (d) to step (b) and/or (c).

7. The process of claim 1, wherein the liquid stream produced in step (a) has a concentration of formic acid plus tertiary amine (I) of from 1 to 99% by weight, based on the total amount of the stream.

8. The process of claim 1, wherein the degree of separation in the distillation apparatus of step (c) is selected so that the molar ratio of formic acid to tertiary amine (I) in the bottom output is from 0.1 to 2.0.

9. The process of claim 1, wherein the radicals $R^1$ to $R^3$ are independently selected from the group consisting of $C_1$-$C_{12}$-alkyl, $C_5$-$C_8$-cycloalkyl, benzyl, and phenyl.

10. The process of claim 1, wherein the radicals $R^1$ to $R^3$ are independently selected from the group consisting of $C_5$-$C_8$-alkyl.

* * * * *